US010877655B1

(12) United States Patent
Hay et al.

(10) Patent No.: US 10,877,655 B1
(45) Date of Patent: Dec. 29, 2020

(54) METHOD OF ANALYZING, DISPLAYING, ORGANIZING AND RESPONDING TO VITAL SIGNALS

(71) Applicant: RDI TECHNOLOGIES, INC., Knoxville, TN (US)

(72) Inventors: Jeffrey R. Hay, Louisville, KY (US); Jenna L. Johns, Knoxville, TN (US)

(73) Assignee: RDI TECHNOLOGIES, INC., Knoxville, TN (US)

( * ) Notice: Subject to any disclaimer, the term of this patent is extended or adjusted under 35 U.S.C. 154(b) by 0 days.

(21) Appl. No.: 16/165,252

(22) Filed: Oct. 19, 2018

Related U.S. Application Data

(63) Continuation of application No. 14/757,256, filed on Dec. 9, 2015, now Pat. No. 10,108,325.
(Continued)

(51) Int. Cl.
*G06K 9/00* (2006.01)
*G06F 3/0484* (2013.01)
(Continued)

(52) U.S. Cl.
CPC ........ *G06F 3/04847* (2013.01); *A61B 5/0077* (2013.01); *A61B 5/01* (2013.01); *A61B 5/024* (2013.01); *A61B 5/0816* (2013.01); *A61B 5/165* (2013.01); *A61B 5/4815* (2013.01); *A61B 5/7435* (2013.01); *G01N 29/44* (2013.01); *G06F 16/7335* (2019.01); *G06K 9/00335* (2013.01); *G06K 9/00771* (2013.01); *G06T 7/0016* (2013.01); *G06T 7/11* (2017.01); *G06T 7/248* (2017.01); *G06T 7/262* (2017.01); *G01N 2291/028* (2013.01); *G06T 2200/24* (2013.01); *G06T 2207/10016* (2013.01); *G06T 2207/20056* (2013.01); *G06T 2207/20216* (2013.01);
(Continued)

(58) Field of Classification Search
None
See application file for complete search history.

(56) References Cited

U.S. PATENT DOCUMENTS 5,517,251 A 5/1996 Rector et al.
5,666,157 A 9/1997 Aviv
(Continued)

OTHER PUBLICATIONS

Liebold et al. "Contact-less human vital sign monitoring with a 12 channel synchronous parallel processing magnetic impedance measurement system", Springer (Year: 2009).*
(Continued)

*Primary Examiner* — Randolph I Chu
(74) *Attorney, Agent, or Firm* — Wyatt, Tarrant & Combs, LLP; Stephen C. Hall

(57) ABSTRACT

A system for monitoring vital signs includes: an imaging device for acquiring video image files of a living individual; a data analysis system including a processor and memory; a computer program running in the data analysis system to automatically analyze the video images, autonomously identify an area in the images where periodic movements associated with a selected vital sign may be detected and quantified; and, an interface that outputs an electrical signal corresponding to the waveform of the selected vital sign. The system may include a Graphical User Interface, which may display a visual graph of the waveform and a single video frame or a video stream of the individual.

21 Claims, 35 Drawing Sheets

Related U.S. Application Data

(60) Provisional application No. 62/209,979, filed on Aug. 26, 2015, provisional application No. 62/161,228, filed on May 13, 2015, provisional application No. 62/154,011, filed on Apr. 28, 2015, provisional application No. 62/139,110, filed on Apr. 14, 2015, provisional application No. 62/146,744, filed on Apr. 13, 2015, provisional application No. 62/141,940, filed on Apr. 2, 2015, provisional application No. 62/139,127, filed on Mar. 27, 2015, provisional application No. 62/090,729, filed on Dec. 11, 2014.

(51) Int. Cl.

| | | |
|---|---|---|
| *G06T 7/11* | (2017.01) | |
| *G06T 7/246* | (2017.01) | |
| *G06T 7/262* | (2017.01) | |
| *G01N 29/44* | (2006.01) | |
| *A61B 5/00* | (2006.01) | |
| *G06T 7/00* | (2017.01) | |
| *A61B 5/16* | (2006.01) | |
| *A61B 5/01* | (2006.01) | |
| *A61B 5/024* | (2006.01) | |
| *A61B 5/08* | (2006.01) | |
| *G06F 16/732* | (2019.01) | |
| *H04N 7/18* | (2006.01) | |

(52) U.S. Cl.
CPC ........... *G06T 2207/30004* (2013.01); *G06T 2207/30164* (2013.01); *H04N 7/18* (2013.01)

(56) References Cited

U.S. PATENT DOCUMENTS

| | | | |
|---|---|---|---|
| 6,028,626 A | 2/2000 | Aviv | |
| 6,295,383 B1 | 9/2001 | Smitt et al. | |
| 6,422,741 B2 | 7/2002 | Murphy et al. | |
| 6,727,725 B2 | 4/2004 | Devaney et al. | |
| 6,774,601 B2 | 8/2004 | Schwartz et al. | |
| 6,792,811 B2 | 9/2004 | Argento et al. | |
| 7,622,715 B2 | 11/2009 | Ignatowicz | |
| 7,672,369 B2 | 3/2010 | Garakani et al. | |
| 7,710,280 B2 | 5/2010 | McLellan | |
| 7,862,188 B2 | 1/2011 | Luty et al. | |
| 7,903,156 B2 | 3/2011 | Nobori et al. | |
| 8,119,986 B1 | 2/2012 | Garvey, III et al. | |
| 8,149,273 B2 | 4/2012 | Liu et al. | |
| 8,170,109 B2 | 5/2012 | Gaude et al. | |
| 8,242,445 B1 | 8/2012 | Scanlon et al. | |
| 8,351,571 B2 | 1/2013 | Brinks et al. | |
| 8,374,498 B2 | 2/2013 | Pastore | |
| 8,475,390 B2 | 7/2013 | Heaton et al. | |
| 8,483,456 B2 | 7/2013 | Nagatsuka et al. | |
| 8,502,821 B2 | 8/2013 | Louise et al. | |
| 8,515,711 B2 | 8/2013 | Mitchell et al. | |
| 8,526,674 B2 | 9/2013 | Patti | |
| 8,537,203 B2 | 9/2013 | Seibel et al. | |
| 8,693,735 B2 | 4/2014 | Kielkopf et al. | |
| 8,720,781 B2 | 5/2014 | Wang et al. | |
| 8,731,241 B2 | 5/2014 | Johnson et al. | |
| 8,765,121 B2 | 7/2014 | Maslowski | |
| 8,774,280 B2 | 7/2014 | Tourapis et al. | |
| 8,797,439 B1 | 8/2014 | Coley et al. | |
| 8,803,977 B2 | 8/2014 | Uchima et al. | |
| 8,811,708 B2 | 8/2014 | Fischer et al. | |
| 8,823,813 B2 | 9/2014 | Mantzel et al. | |
| 8,831,370 B2 | 9/2014 | Archer | |
| 8,874,374 B2 | 10/2014 | Bogucki | |
| 8,879,789 B1 | 11/2014 | Figov et al. | |
| 8,879,894 B2 | 11/2014 | Neuman et al. | |
| 8,884,741 B2 | 11/2014 | Cavallaro et al. | |
| 8,897,491 B2 | 11/2014 | Ambrus et al. | |
| 8,924,163 B2 | 12/2014 | Hudson et al. | |
| 9,006,617 B2 | 4/2015 | Mullen | |
| 9,075,136 B1 | 7/2015 | Joao | |
| 9,448,205 B2 * | 9/2016 | Igney | G01N 27/023 |
| 2004/0032924 A1 | 2/2004 | Judge, Jr. | |
| 2004/0081369 A1 | 4/2004 | Gindele et al. | |
| 2004/0160336 A1 | 8/2004 | Hoch et al. | |
| 2006/0009700 A1 | 1/2006 | Brumfield et al. | |
| 2006/0049707 A1 | 3/2006 | Vuyyuru | |
| 2007/0061043 A1 | 3/2007 | Ermakov et al. | |
| 2007/0276270 A1 | 11/2007 | Tran | |
| 2009/0010570 A1 | 1/2009 | Yamada et al. | |
| 2010/0033579 A1 | 2/2010 | Yokohata et al. | |
| 2010/0042000 A1 | 2/2010 | Schuhrke et al. | |
| 2010/0091181 A1 | 4/2010 | Capps | |
| 2010/0328352 A1 | 12/2010 | Shamir et al. | |
| 2011/0019027 A1 | 1/2011 | Fujita et al. | |
| 2011/0152729 A1 | 6/2011 | Oohashi et al. | |
| 2012/0207218 A1 | 8/2012 | Asamura et al. | |
| 2013/0060571 A1 | 3/2013 | Soemo et al. | |
| 2013/0176424 A1 | 7/2013 | Weil | |
| 2013/0201316 A1 | 8/2013 | Binder et al. | |
| 2013/0342691 A1 | 12/2013 | Lewis et al. | |
| 2014/0002667 A1 | 1/2014 | Cheben et al. | |
| 2014/0072190 A1 | 3/2014 | Wu et al. | |
| 2014/0072228 A1 | 3/2014 | Rubinstein et al. | |
| 2014/0072229 A1 | 3/2014 | Wadhwa et al. | |
| 2014/0112537 A1 | 4/2014 | Frank et al. | |
| 2014/0169763 A1 | 6/2014 | Nayak et al. | |
| 2014/0205175 A1 | 7/2014 | Tanaka et al. | |
| 2014/0236036 A1 | 8/2014 | de Haan et al. | |
| 2014/0275832 A1 * | 9/2014 | Muehlsteff | A61B 5/02416 600/301 |
| 2014/0334697 A1 * | 11/2014 | Kersten | A61B 5/02416 382/128 |
| 2014/0341470 A1 | 11/2014 | Lee et al. | |
| 2015/0005646 A1 * | 1/2015 | Balakrishnan | A61B 5/0255 600/479 |
| 2015/0134545 A1 | 5/2015 | Mann et al. | |
| 2015/0221534 A1 | 8/2015 | van der Meulen | |
| 2016/0217587 A1 | 7/2016 | Hay | |

OTHER PUBLICATIONS

Abbas et al. "Neonatal non-contact respiratory monitoringbased on real-time infrared thermography", BioMed Central. (Year: 2011).*

Philips, "Philips launches update to Vital Signs Camera app" (Year: 2012).*

Fei et al. , "Thermal Vision for Sleep Apnea Monitoring", pp. 1084-1091 (Year: 2009).*

Wadhwa et al., "Phase-based Video Motion Processing", also see YouTube https://www.youtube.com/watch?v=W7ZQ-FG7Nvw, SIGGRAPH 2013.

Wu et al., "Eulerian Video Magnification for Revealing Subtle Changes in the World", ACM Transactions on Graphics (TOG)—Proceedings of ACM SIGGRAPH 2012 TOG Homepag, evolume 31 issue 4, Jul. 2012, Article No. 65.

Liu et al., "Motion magnification", ACM Transactions on Graphics (TOG)—Proceedings of ACM SIGGRAPH 2005 TOG Homepage, vol. 24 Issue 3, Jul. 2005.

Rubinstein et al. ("Revealing Invisible Changes in the world (YouTube)", YouTube, https://www.youtube.com/watch?v=e9ASH8IBJ2U, 2012.

Rubinstein et al. ("Eulerian Video Magnification" (YouTube), YouTube https://www.youtube.com/watch?v=ONZcjs1Pjmk, 2012).

Hay, JR, "High Dynamic Range Imaging for the Detection of Motion", pp. 18-141; dissertation University of Louisville (Kentucky); May 2011.

Mazen, et al.; A vision-based approach for the direct measurement of displacements in vibrating systems; article from Smart Materials and Structures; 2003; 12; pp. 785-794; IOP Publishing LTD; UK.

* cited by examiner

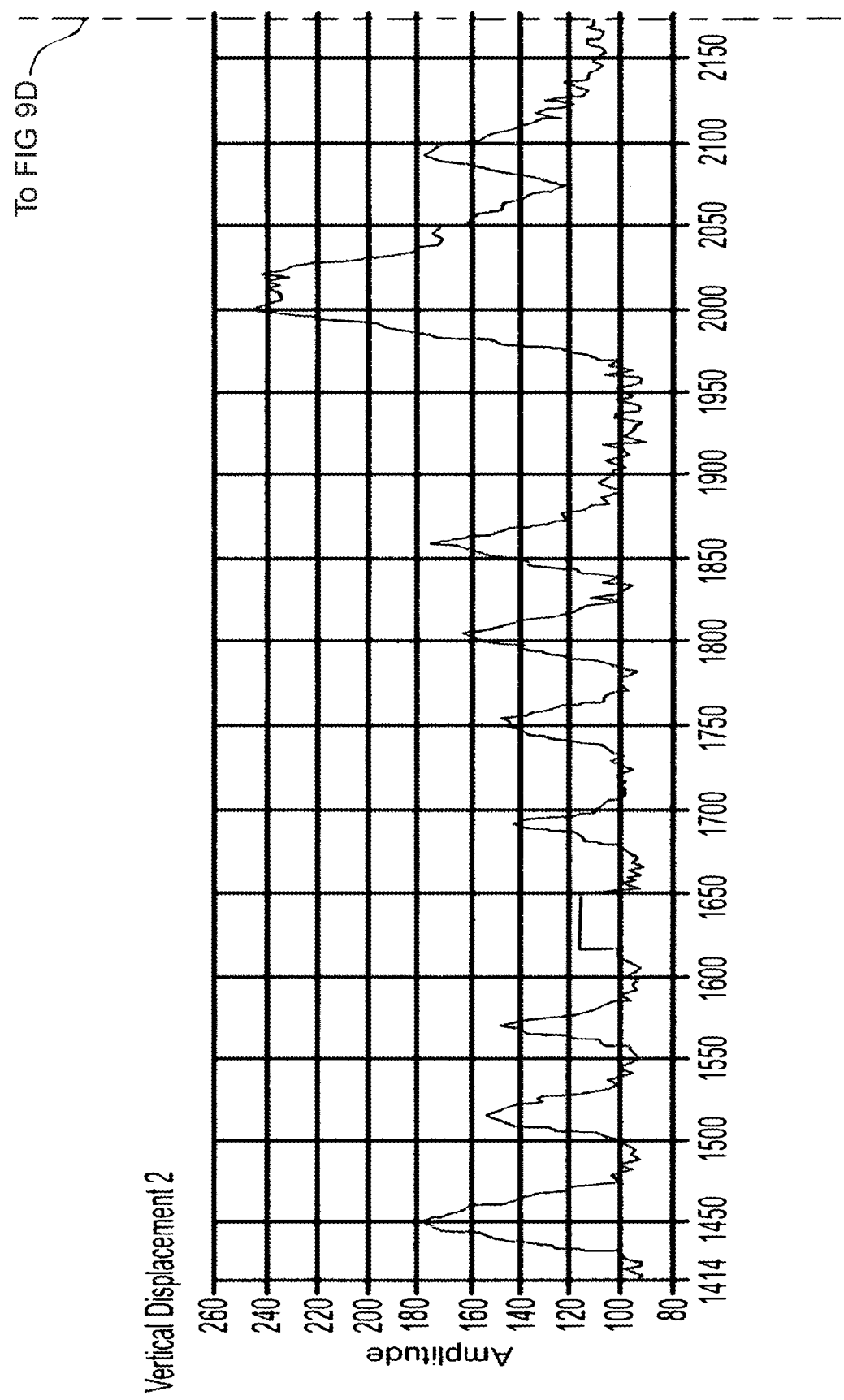

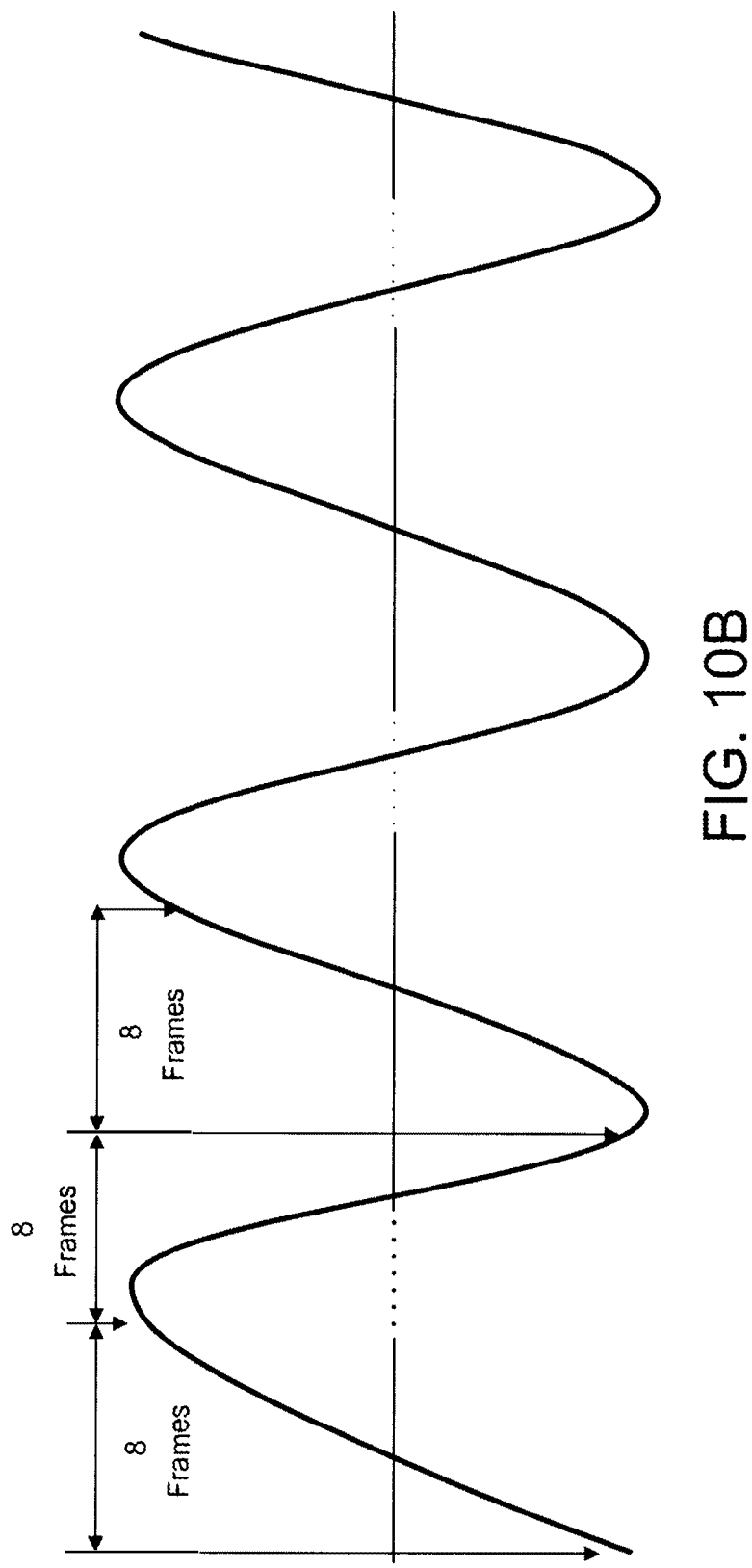

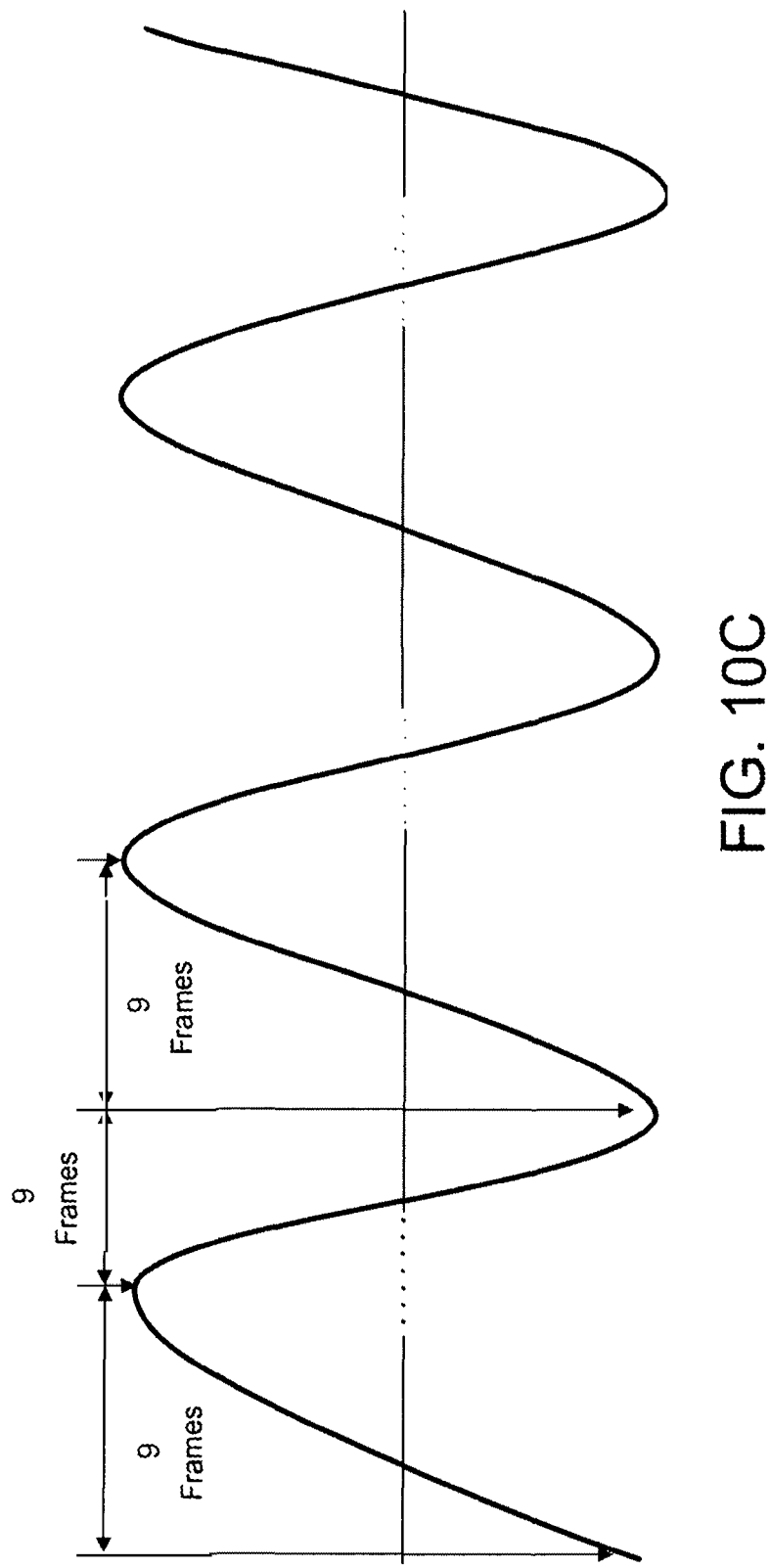

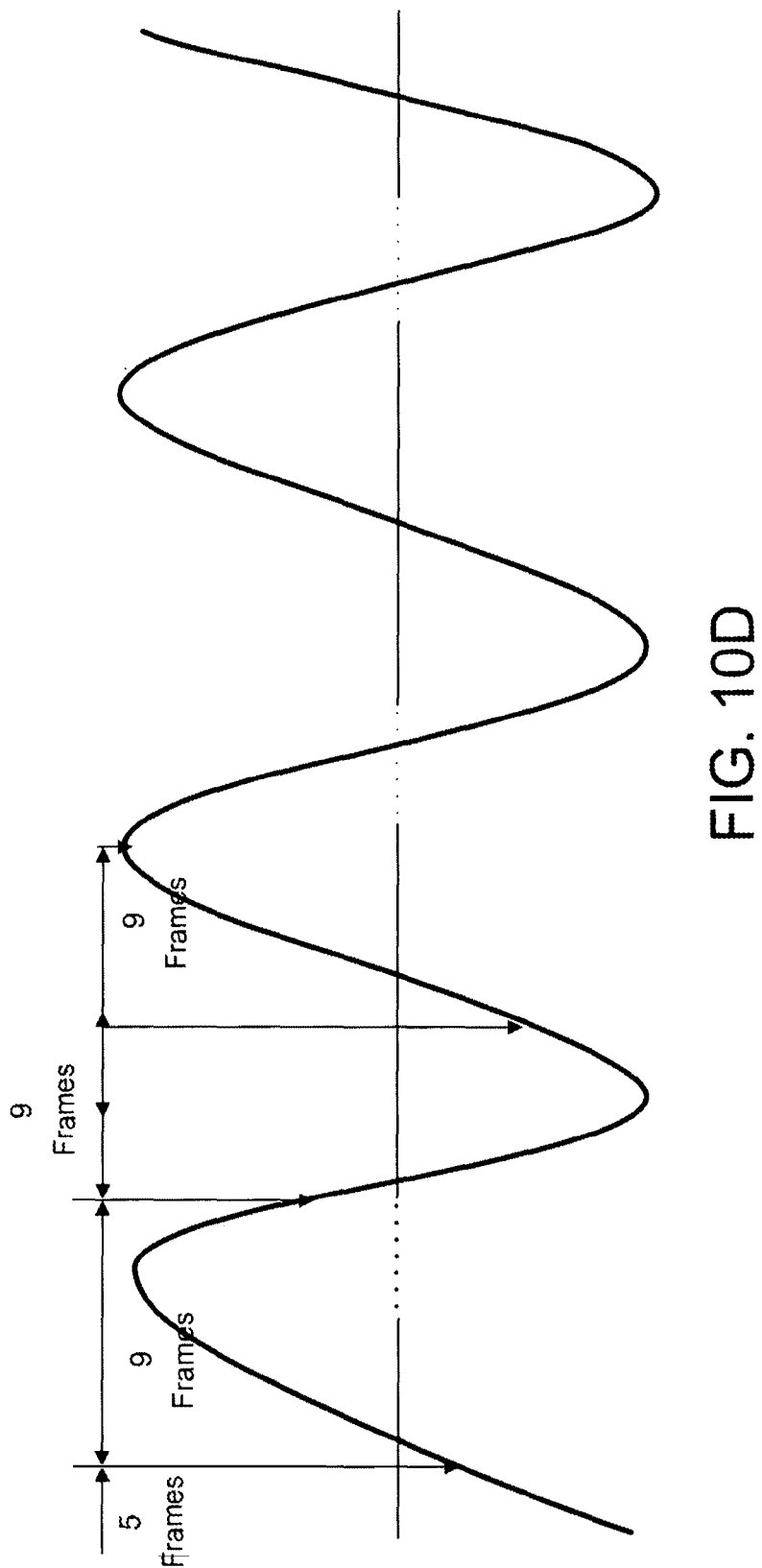

FIG. 12A
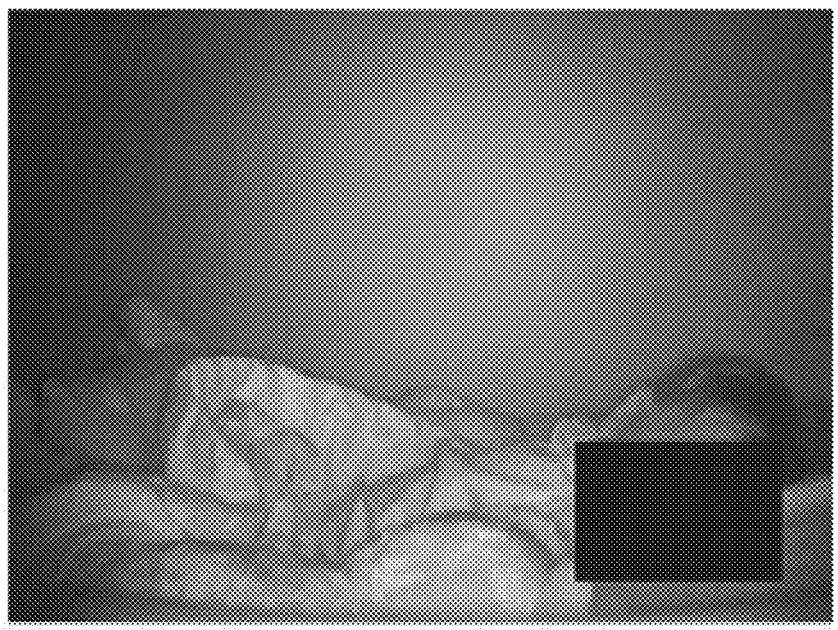
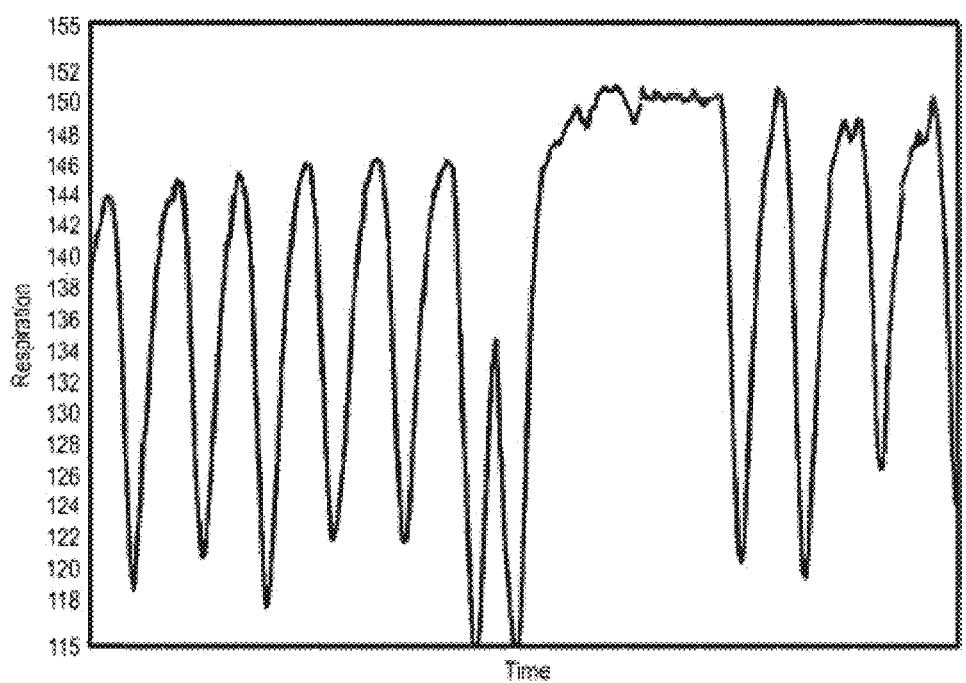
FIG. 12B

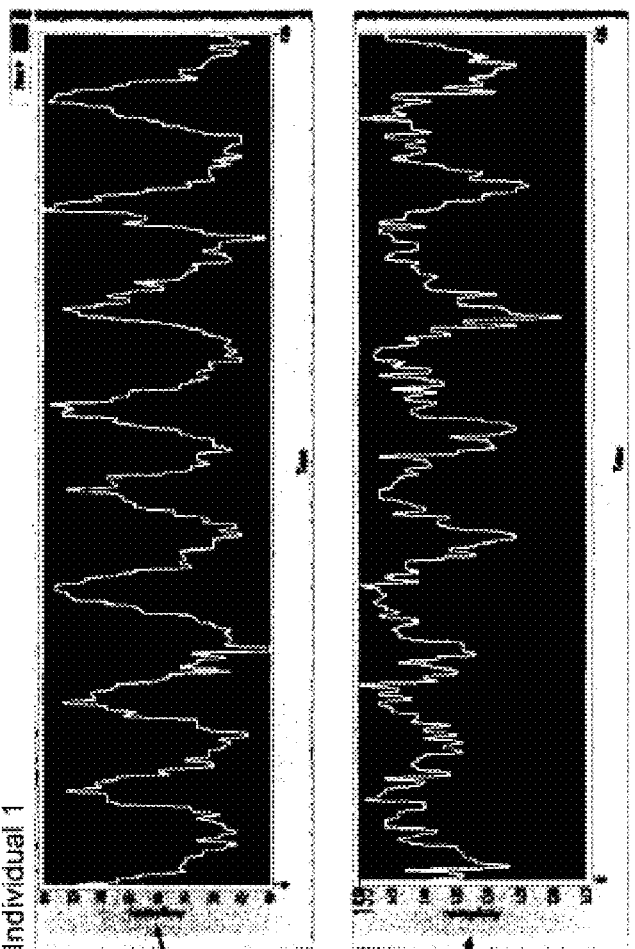
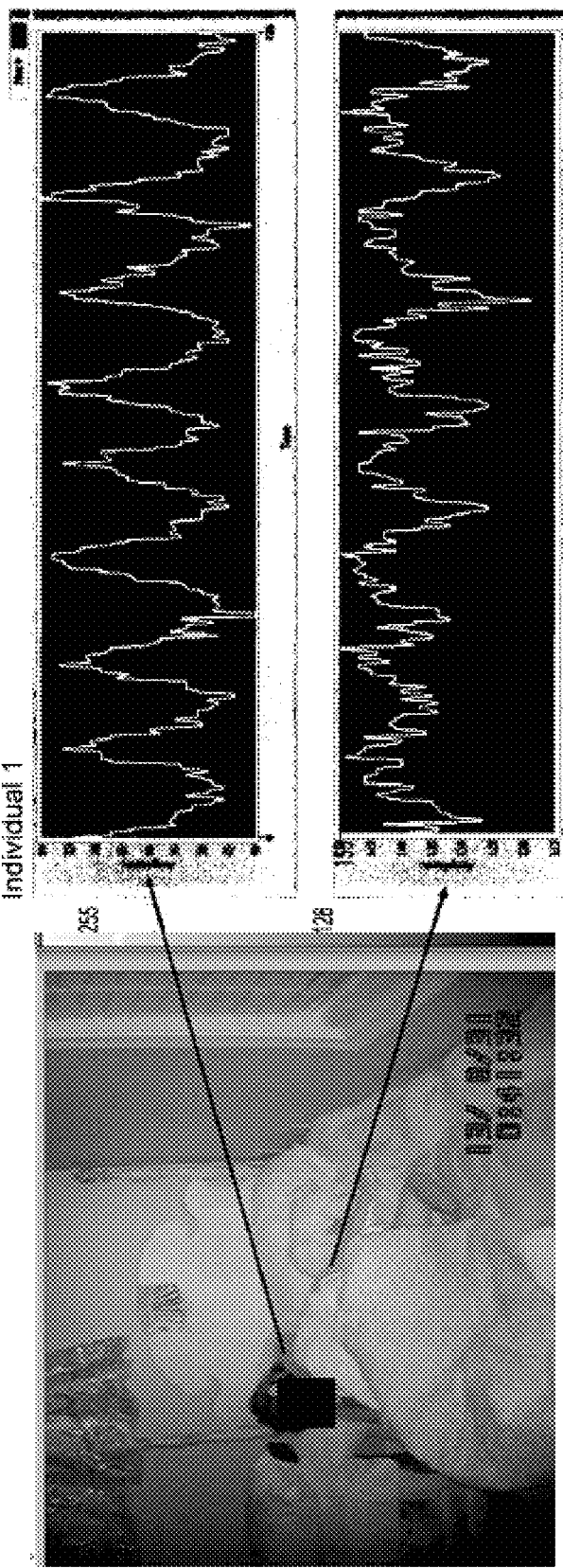
FIG. 15B  FIG. 15C  FIG. 15A

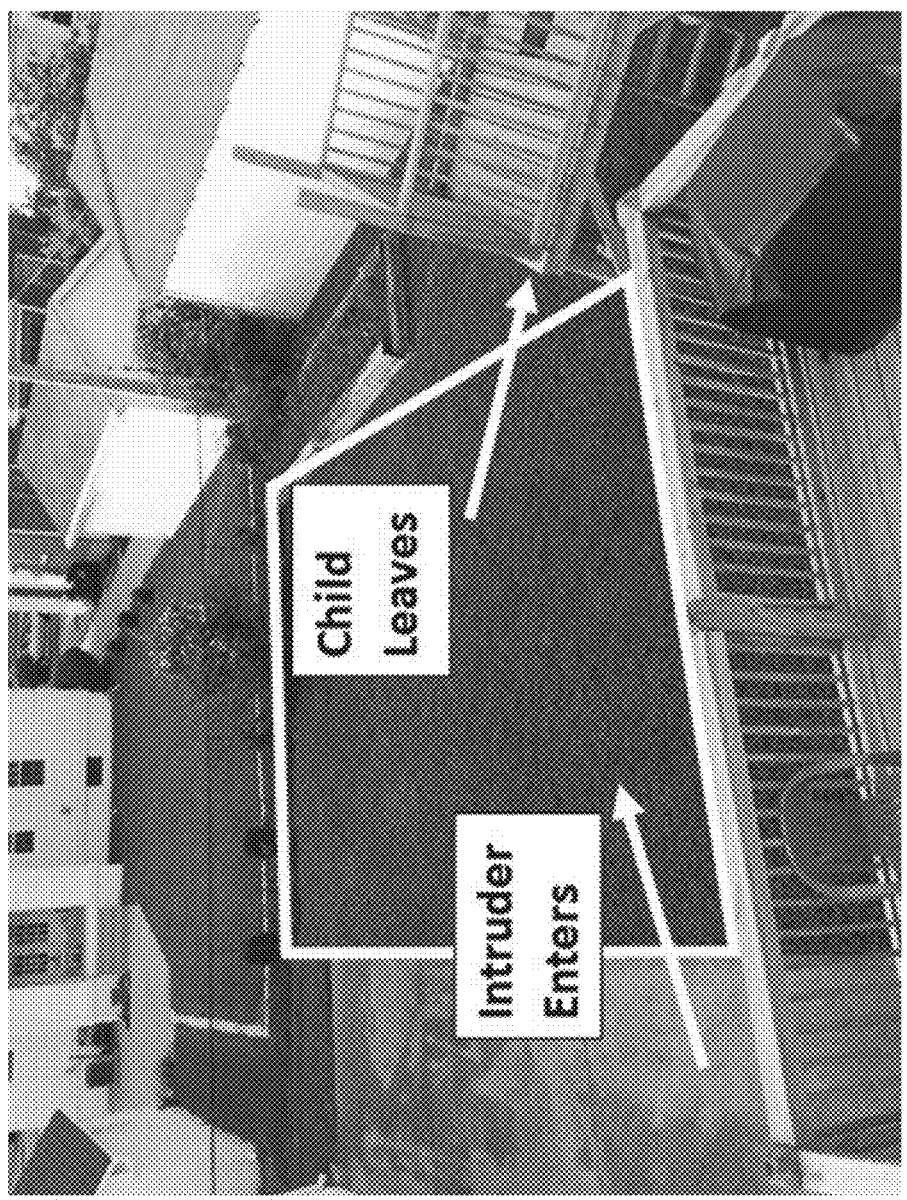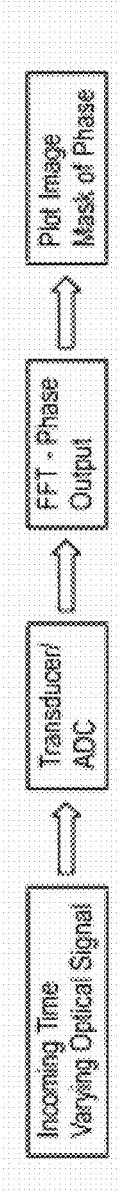
FIG. 26
FIG. 27

METHOD OF ANALYZING, DISPLAYING, ORGANIZING AND RESPONDING TO VITAL SIGNALS

CROSS REFERENCE TO RELATED U.S. APPLICATIONS

This application is a continuation of, and claims priority to, application Ser. No. 14/757,256, filed Dec. 9, 2015, and published on Jul. 21, 2016 as U.S. Publication No. 2016/0210747, titled "Method of analyzing, displaying, organizing and responding to vital signals," which itself claimed the benefit of each of the following Provisional Patent Application Ser. No. 62/209,979, "Comparative analysis of time-varying and static imagery in a field", filed on Aug. 26, 2015; Ser. No. 62/161,228, "Multiple region perimeter tracking and monitoring", filed on May 13, 2015; Ser. No. 62/154,011, "Non contact optical baby monitor that senses respiration rate and respiratory waveform", filed on Apr. 28, 2015; Ser. No. 62/139,110, "Adaptive array comparison", filed on Apr. 14, 2015; Ser. No. 62/146,744, "Method of analyzing, displaying, organizing, and responding to vital signals", filed on Apr. 13, 2015; Ser. No. 62/141,940, "Method and system for analysis of structures and objects from spatio-temporal data", filed on Apr. 2, 2015; Ser. No. 62/139,127, "Method for determining, comparing, measuring, and displaying phase", filed on Mar. 27, 2015; and Ser. No. 62/090,729, "Optical detection of periodic movement", filed on Dec. 11, 2014, the disclosures of each of which are incorporated herein by reference in their entirety.

The parent application (Ser. No. 14/757,256, patented as U.S. Pat. No. 10,108,325) is related to the following: "Non-contacting monitor for bridges and civil structures," Ser. No. 14/757,255 filed Dec. 9, 2015 and issued as U.S. Pat. No. 9,704,266 on Jul. 11, 2017; "Method of analyzing periodic motions in machinery," Ser. No. 14/757,245 filed Dec. 9, 2015 and published as U.S. Publication No. 2016/0217587 on Jul. 28, 2016; and "Method of adaptive array comparison for the detection and characterization of periodic motion", Ser. No. 14/757,259 filed Dec. 9, 2015 and published as U.S. Publication No. 2016/0217588 on Jul. 28, 2016, the entire disclosures of each and every one of which is incorporated herein by reference.

BACKGROUND

1. Field of the Invention

The invention pertains to apparatus and methods for monitoring the vital signs of a patient. More specifically, the invention pertains to a non-contacting video-based analysis system to monitor to determine a person's presence, for example the existence of vital signs in a controlled space where no one is supposed to be.

2. Description of Related Art

Respiration rate is an important vital sign. Manual methods of determining respiration rate are intermittent and have proven to be unreliable. Continuous methods have limitations; either they are not accurate or are poorly tolerated by patients. Respiration rate is a key indicator of ventilation. Abnormal respiration rate, either too high (tachypnea), too low (bradypnea), or absent (apnea), is a sensitive indicator of physiologic distress that requires immediate clinical intervention.

The most common method for respiration rate measurement is by physical assessment, either by counting chest wall movements or by auscultation of breath sounds with a stethoscope. Many studies have shown manual methods to be unreliable in acute care settings, especially on the general care floor, where the majority of patients receive care. Even if they were reliable, manual methods are limited by their intermittent nature.

Two continuous methods for respiration rate monitoring are used in multiparameter monitors, viz., thoracic impedance pneumography and capnography monitoring.

The thoracic chest wall expands and contracts during the respiratory cycle from which respiration rate can be determined by measuring changes in electrical impedance associated with this movement. Monitoring of respiration rate by thoracic impedance is convenient if the patient is already monitored for ECG, but the method is prone to inaccurate readings due to a number of factors including: ECG electrode placement, motion artifacts, and physiologic events non-related to respiration rate that cause chest wall movement (e.g. coughing, eating, vocalization, crying).

Continuous end tidal $CO_2$ monitoring with capnography is the standard of care in surgical settings to establish end tracheal intubation. Since intubated patients have a clear respiratory pattern without entrainment of room air, it is easy for the capnometer to report the respiration rate. However, capnometers that continuously monitor ventilation for non-intubated patients require a nasal airway cannula that draws a continuous gas sample for spectrographic measurements within the capnometer. Capnometry measurement of respiration rate is the most frequent method used by anesthesiologists. This method is sensitive to central, obstructive, and mixed apneas. The primary limitations of continuous respiration rate monitoring by capnometry are low patient tolerance of the nasal cannula and the added nursing workload to respond to dislodged or clogged cannulas during the patient stay. In addition, any entrainment of room air by the sampling cannula can cause erroneous end-tidal values. A recent study of pediatric patients showed premature cannula dislodgement in 14 out of the 16 patients enrolled in the study.

There is a clear demand for improved methods for respiration monitoring: For general baby monitors, no reliable product exists that can measure respiration without a pad under the bed/child or attachment on the child's diaper or clothing. Reliable monitors are needed, in particular, to address the so-called Sudden Infant Death Syndrome (SIDS). According to the CDC, every year in the U.S., more than 4,500 infants die suddenly of no obvious cause. A significant portion of these deaths are sleep related, where a perfectly healthy baby simply stops breathing in his/her sleep without warning. Other sleep related disorders affect large numbers of people. For example, more than 15% of adolescents complain of some form of sleep problems, many of which may contribute to misdiagnosis of ADHD and other behavioral problems.

Improved monitoring is needed in the hospital environment as well. In spite of its clinical importance, respiration rate is the last core vital sign without a reliable and continuous monitoring solution that patients can easily tolerate. The lack of a reliable respiration rate measurement is a major contributor to avoidable adverse events. One retrospective study of over 14,000 cardiopulmonary arrests in acute care hospitals showed 44% were of respiratory origin. Another study reported that respiratory failure, a key Patient Safety Indicator (PSI), has increased in U.S. Acute Care Hospitals. The reported incidence is 17.4 per 1,000 hospital admissions, leading to over 15,000 avoidable deaths at a cost to the healthcare system of over $1.8 billion.

Objects and Advantages

Objects of the present invention include the following: providing an improved system and method for measuring respiration rate; providing a non-contacting respiration monitor that is reliable under normal sleeping conditions; providing a stand-off monitor for vital signs; providing a method to extract respiration rate from a video file; providing a graphical user interface that displays respiration data; providing a user interface that directly associates respiration with a video stream so that selected events may be time-stamped and associated with corresponding frames of the video image; and providing an improved tool for detecting sleep apnea, analyzing different types of apnea, and warning of SIDS-related events in real time. These and other objects and advantages of the invention will become apparent from consideration of the following specification, read in conjunction with the drawings.

SUMMARY

According to one aspect of the invention, a system for monitoring vital signs comprises:
 a device for acquiring video image files;
 a data analysis system including a processor and memory;
 a computer program to automatically analyze the video images, identify an area in the images where periodic movements associated with a selected vital sign may be detected and quantified; and,
 a user interface in which the temporal variation of at least one vital sign may be displayed along with at least one video frame corresponding to a selected time in the temporal variation display.

According to another aspect of the invention, a system for monitoring vital signs comprises:
 a device for acquiring video image files;
 a data analysis system including a processor and memory;
 a computer program to automatically analyze the video images, identify an area in the images where periodic movements associated with a selected vital sign may be detected and quantified; and,
 an interface that outputs an electrical signal corresponding to the waveform of the selected vital sign.

According to another aspect of the invention, a system for monitoring vital signs comprises:
 a device for acquiring video image files;
 a data analysis system including a processor and memory;
 a computer program to automatically analyze the video images, identify an area in the images where periodic movements associated with a selected vital sign may be detected, and quantify the rate of periodic movements using an adaptive array comparison method; and,
 a user interface in which the temporal variation of at least one vital sign may be displayed.

According to another aspect of the invention, a method for monitoring vital signs comprises the steps of:
 acquiring video image files of an individual;
 in a data analysis system including a processor and memory, using a computer program to:
 automatically analyze the video images, autonomously identify an area in the images where periodic movements associated with a selected vital sign may be detected, and
 quantify the rate of periodic movements using an adaptive array comparison method; and,
 displaying the temporal variation of at least one vital sign on a user interface.

According to another aspect of the invention, a method for monitoring vital signs comprises the steps of:
 acquiring video image files of an individual;
 using a computer program in a data analysis system including a processor and memory, to:
 automatically analyze the video images,
 autonomously identify an area in the images where periodic movements associated with a selected vital sign may be detected,
 quantify the rate of periodic movements using an adaptive array comparison method, and,
 store the quantified data and the video image file with a common time log so that particular changes in periodicity of the vital sign may be associated with corresponding video frames; and,
 displaying the temporal variation of at least one vital sign on a user interface.

According to another aspect of the invention, a system for monitoring vital signs comprises:
 a device for acquiring video image files;
 a data analysis system including a processor and memory;
 a computer program to automatically analyze the video images, autonomously identify an area in the images within a preselected perimeter where periodic movements associated with a selected vital sign may be detected, and quantify the rate of periodic movements using an adaptive array comparison method; and,
 a user interface in which the temporal variation of at least one vital sign may be displayed.

BRIEF DESCRIPTION OF DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting embodiments illustrated in the drawing figures, wherein like numerals (if they occur in more than one view) designate the same elements. The features in the drawings are not necessarily drawn to scale.

FIGS. 9C and 9D illustrate one irregular and transient event in an otherwise periodic motion.

FIGS. 10A-10D illustrate the steps in an exemplary analysis for the specific case of respiration, wherein 10A shows 4-frame spacing, 10B shows 8-frame spacing, 10C shows 9-frame spacing, and 10D shows 9-frame spacing but with a 5-frame offset.

FIG. 12A illustrates an infant and FIG. 12B illustrates the respiration waveform of the pictured infant from FIG. 12A in which breathing stopped for a short period.

FIG. 15A illustrates a mother and a child sleeping together. FIG. 15B illustrates the successful capture of individual respiratory waveforms from mother (Individual 1) and FIG. 15C illustrates the successful capture of individual respiratory waveforms from child (Individual 2), using the present invention.

FIG. 26 shows the use of a user-defined perimeter in an outdoor environment.

FIG. 27 illustrates schematically one sequence of steps for determining and displaying phase in accordance with one aspect of the invention.

MULTIPLE EMBODIMENTS AND ALTERNATIVES

Figure 1:
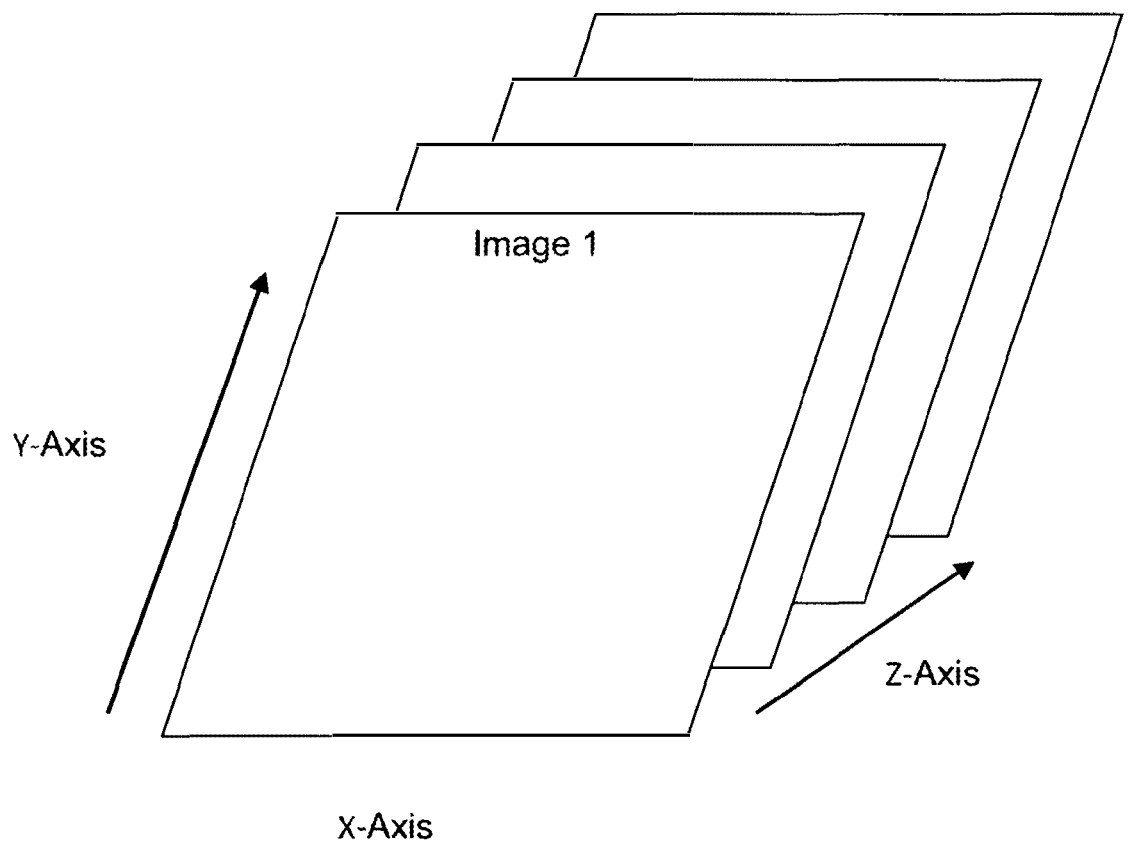
FIG. 1 illustrates schematically the arrangement of video data into a three-dimensional array where x, y are spatial coordinates in a video image and z is time.

In its most general sense, the invention comprises a video-based system for observing a patient, and using a processor to: first, identify areas of a video image that represent periodic movement associated with a vital sign, such as respiration or pulse rate, second, to quantify and track the periodic movement, and third, to output data related to the periodic movement through a selected user interface. The user interface may be a dedicated interface, for instance, to use in a hospital or acute care setting. Alternatively it may consist of a software application configured to operate on a mobile device, for instance, if a parent or caregiver needs to monitor a sleeping infant. The data stream may be presented in real time as a simple display of respiration rate, pulse rate, etc., or it may be archived for later review. Archived data are preferably time-stamped so that any selected part of the derived data may be associated with the respective video frame(s) corresponding to the selected time. A user interface may allow the user to display data for a selected time interval and then select a particular time within that interval, for which the corresponding video frame will be displayed. Alternatively, an interface may output a signal that represents the respiration waveform. The output signal may be in any convenient analog or digital format, e.g., 0-5 V, 4-20 mA, and may be part of a network, wireless network, mesh network, or other control and automation system operating on any convenient protocol, e.g, HART, WirelessHART, ZigBee, IEEE 802.15.4, etc.

It will be appreciated that many "video cameras" and "video recordings" include not only images but also the corresponding audio data, synchronized with the image data. The invention can make use of the associated audio data in a number of ways, as will be described in several Examples.

It will be appreciated that the term "patient" or "individual" is used herein for convenience, and is intended to cover any human or animal that is to be monitored for vital signs. The term "patient" does not necessarily imply that the individual is ill or is presently undergoing medical treatment. Some non-limiting examples include: a sleeping infant being monitored for sleep apnea, SIDS, or other signs of distress; a patient in a hospital, emergency room, or nursing home; a patient undergoing study for sleeping disorders; a soldier in a combat situation; a person in a crowd being monitored for signs of stress or communicable disease; or an animal under veterinary care.

The invention may be conveniently integrated into currently available video monitors to derive real-time information such as respiration rate, cessation of breathing, respiration waveform, and motion events. It can also study more than one individual in a video file and separate their individual waveforms for analysis. It can also be easily integrated with any camera that has infrared technology and recording capability. The user interface may display real-time information (video and graphs) to display respiration rate, cessation of breathing events, the actual respiration waveform, and motion events. The data, and associated video frame(s) can provide visual feedback on the quality of a patient's sleep, while identifying potential issues such as central and obstructive sleep apnea, breathing cessation, and sleep inhibitors. It can also be used for post-surgery assessment of the impact on sleep. Further, the data may be conveniently structured to produce reports and visuals that better inform parents of potential sleep related issues that need to be addressed during visits to the pediatrician.

In the examples that follow, various aspects of the invention will be made clearer, and applications to various monitoring problems will be illustrated. These examples are not intended to restrict the scope of the invention to the particular implementations described. In some exemplary renderings of the user interface, the identity of the patient has been obscured for the purposes of inclusion in this disclosure; however, it will be understood that in an actual clinical setting the face of the patient would typically be visible to some degree in the video images and not obscured or blacked out as it is herein.

Method of Adaptive Array Comparison

Example

One way to analyze a video stream to extract waveform information is Adaptive Array Comparison, which may be described generally as follows: A video signal includes multiple frames separated in time and each frame includes multiple pixels. Each pixel value in a particular frame is compared to the values of corresponding pixels in different frames of the video signal to search for periodic signals occurring at the pixel locations over time. Periodic signals are defined in time with a maximum and minimum peaks. These two locations give the maximized absolute value in the difference in two locations of the periodic signals. This fact can be exploited to filter and locate pixel locations where the periodic signal gives the largest signal to background or signal-to-noise in a scene or image sequence. In the case of human respiration we know the adult rate typically lies in the approximate range of 12-20 breaths per minute. This corresponds to 0.25 to 0.33 Hz. A medium rate would be 16 breaths per minute or 0.27 Hz. For a 15 fps camera that corresponds to a breath every 56.25 frames. This would tell us that a video of a person breathing may include periodic signals at certain pixels having a maximum and minimum at a difference of approximately 28 frames apart. So this could be the initial frame difference the system might use to locate the best pixels to track. The system will difference several series of images at this separation, meaning the value at each pixel location in one frame is subtracted from the value at the corresponding pixel location at a second frame. Then, the second frame is differenced with a third frame and so on. For each pixel location, the absolute values of their differences are added together. Then some number of pixels with the highest sum of differences are selected to be tracked. There is the potential that the chosen frames happen to be 90 degrees (or some other phase shift) out of phase with a max and min; so in the event that no initial peaks are found, the system will recalculate with a 90 degree phase shift (or some other phase shift). Once it has found the correct pixels to track, it will then begin peak counting for each selected pixel, noting the phase of the waveform. Once it has sufficiently determined the precise phase and frequency of the waveform, it will recalibrate, making sure to frame difference such that the number of frames between differences exactly equals the difference between a max and min of the waveform, as well as starting in phase so the difference is aligned with the max and min. The processor runs the code to do this like any other programs, although a specialized piece of hardware specifically designed to do this is not necessarily used (in contrast to the way decoding HD video is typically done).

Applicant has found that the foregoing method adapts to each person's waveform even if it changes. In the example of breathing, different frequency rates can be chosen to start with, based on the age of the individual or previously stored user data. This method inherently filters unwanted frequencies. Because of the selected time difference between frames we reject signals associated with frequencies other than those related to respiration.

Example

An image sequence is obtained through a video camera and stored into memory. A video sequence as shown in FIG. 1 has dimensions of space in the x and y axis while having the dimension of time in the z axis and can be thought of as a 3-D data space. The video sequence contains a periodic or recurring motion of interest that is to be extracted from the data set. For example, a feature of interest may be occurring at a given pixel and we may be interested in monitoring that feature. The system can use its temporal behavior to find and locate that pixel autonomously without any knowledge of the scene, the surrounding pixels, the spatial characteristic of the local pixels or where that pixel may be.

Method of Adaptive Array Comparison for the Detection and Characterization of Periodic Motion Example Mathematical Description:

An image frame is defined as an X-Y matrix. A video file is a set of image frames defining an X-Y-t matrix.

For each pixel (i,j) one can calculate the difference $(D_{i,j})^{M,N}$ between the value at pixel (i,j) in one frame and the value in another frame, where M is the starting frame number and N is the spacing between the two frames. So $(D_{2,3})^{4,9}$ would be the difference in value or intensity at pixel (2,3) in frame 4 compared to that in frame 13.

The difference matrix is then summed (preferably in quadrature) to yield the total difference in pixel intensities between frames M and M+N. Difference matrices are calculated for various values of M and N, to find M and N that give the highest value of summed differences. Then a selected number of pixels (i,j) having the greatest difference are chosen and their intensities are tracked over time to determine the periodicity of movement.

There is generally a limit on how long one does this. For example, at 15 fps for 20 sec there are 300 frames, so if N is 10 the system would difference 29 times (accounting for the ends) or less as M is increased.

Once this is done initially and the system has found the location of a peak and the peak separation it will redo the calibration with a specific M and N to get it exactly on the peak. M would now be the frame number where an expected max or min occurs and N would be the value of ½ of a waveform. This introduces the novel aspect that the process becomes essentially adaptive.

Note that in the preceding Example, the difference matrix was summed in quadrature. Applicants recognize that this is only one of several ways that the values may be combined, such as absolute difference, where the combination of differenced frames has a cumulative effect that increases with more of the desired signal, in this reference motion.

Example

The method and functions of Adaptive Array Comparison may be described as follows:

1. Video Sequence comes in at some frames per second (fps)
2. Some seconds of that data is continually buffered. (Previous frames are overwritten with new frames.) These are the frames that will be processed.
3. From the buffered frames [1], [2], ... [n] a multiple of frame differences N to calculate is selected, e.g. every 4th frame (N=4) or every 5th frame (N=5), etc. This allows the program to find the best periodic motion rate. The time range between frames is selected based on the range of periodic motion we are interested in finding. This also acts as a band pass filter giving preference to the periodic motion rate within this range.
4. The program also offsets these frames, say, starting with the 1st frame, then the second, etc. This allows it to find the best phase. So for example if it is subtracting every 4th frame, it first would do the 1st frame minus the 5th, the 5th minus the 9th, and so on. Then it would do the 2nd frame minus the 6th frame, then the 6th frame minus the 10th.
5. For each test, frame differencing is conducted for some number of frames. For example, 11 frames may be used and 10 frame differences will be calculated. Each frame difference will be an array of absolute value numbers with each position in the array corresponding to a pixel location.
6. After 10 frame differences are calculated the square of the frame difference arrays are added together to produce a total frame difference array. Then the total frame difference array is analyzed to find the array locations having the largest values. For example, the ten largest values in the array may be found and the array locations containing those values are recorded. When subtracting the frames the program adds all the differenced frames from the buffered video in quadrature, meaning it will square the difference values so that negative and positive differences don't cancel. Motion in opposite direction shows up in the difference frame with an opposite sign but for the present purposes it needs to add positively, otherwise back and forth motion can show as zero in the sum of the differenced frames.
7. From all the total frame difference arrays across all the multiples and offsets the program finds a selected number of pixels that have the largest values, say, the brightest 10 pixels. These pixels represent the largest periodic motions in the scene that are between the rate boundaries set in Step 3.
8. Those pixels' values are tracked over time and this will plot the motion waveform. The signals from the tracked pixels are not necessarily in phase. Any two signals could be 180 degrees out of phase and still provide the same information about the existence and the frequency of the same time periodic signal. For example, the signals of all pixels could be out of phase with all other signals, but still correspond to breathing of a subject. Thus the frequency of each signal would be the same.
9. From the motion waveform the system will determine the rate and phase. In terms of frame differencing this translates to the peaks in the waveform occurring every $N^{th}$ frame and the waveform starts at frame M.
10. From the information in Step 9 the Frame Differencing method adapts since it knows where the peaks start and how many frames apart they are.
11. Now it subtracts frames with a separation exactly equal to the separation between a maximum and minimum in the waveform. It will also make sure to start this process exactly on a peak or minimum. This optimizes the rate and phase to precisely select the motion waveform.
12. This process can be repeated based on a number of factors:

a. Time—The method can reiterate every n seconds to ensure it is optimized for the existing waveform.

b. When there is a large excursion in the measured waveform the process can restart as this can be due to a motion event.

c. The process can restart based on a trigger from an external motion detection method.

d. The process can be restarted on buffered data (the 20 seconds of previous video) when an alarm is triggered, (for example, no peaks are detected) to ensure the alarm is accurate. For example, if the waveform is accidentally lost this step could check the last 20 seconds of data to see if the waveform can be detected in another pixel or set of pixels.

It is important to emphasize that the process described above is performed autonomously by the system software without the need for user intervention.

Example

Figure 2:
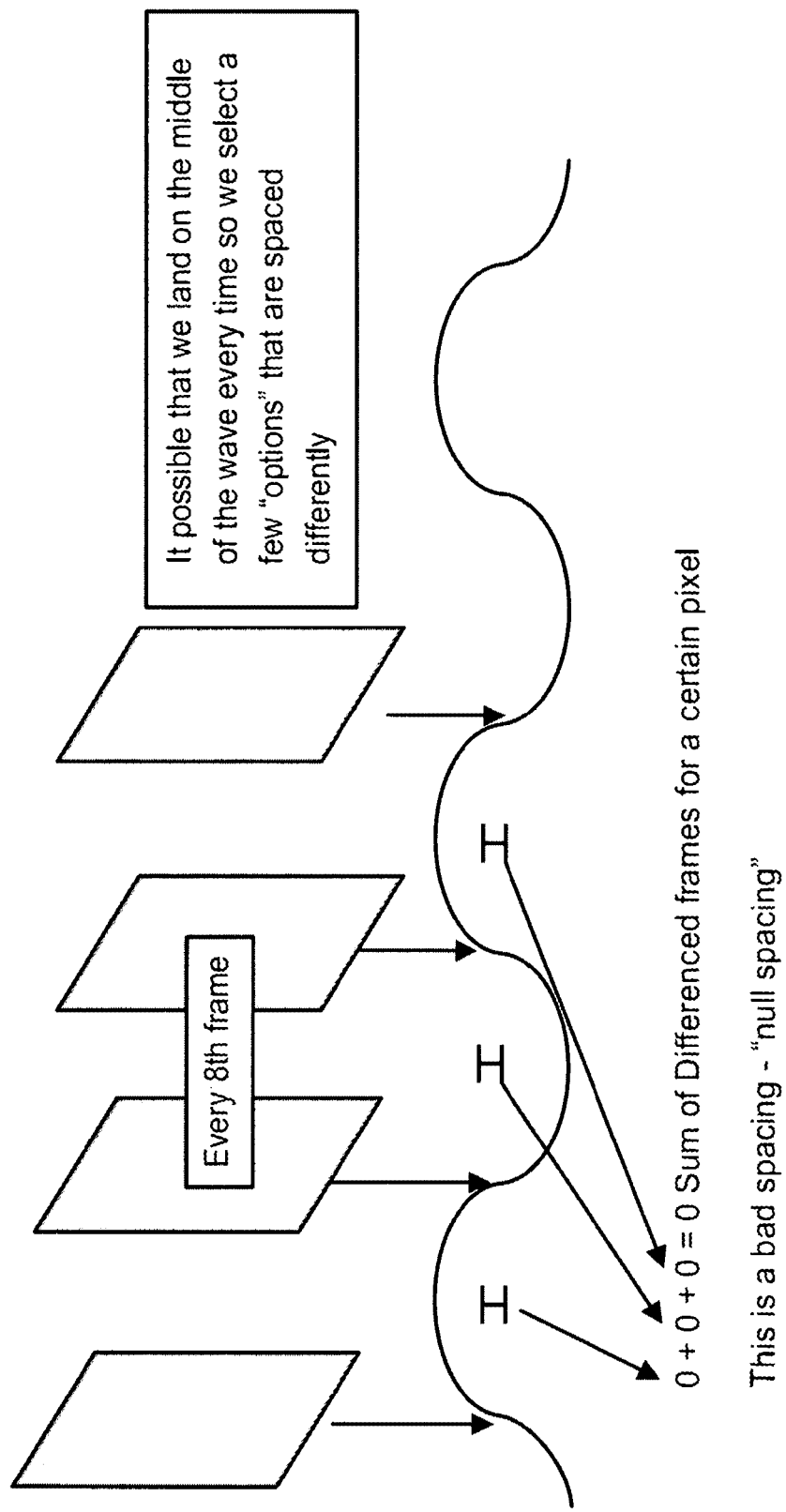
FIG. 2 illustrates the result when the frame spacing is non-optimal, in this case, every 8th frame (N=8).
Figure 3:
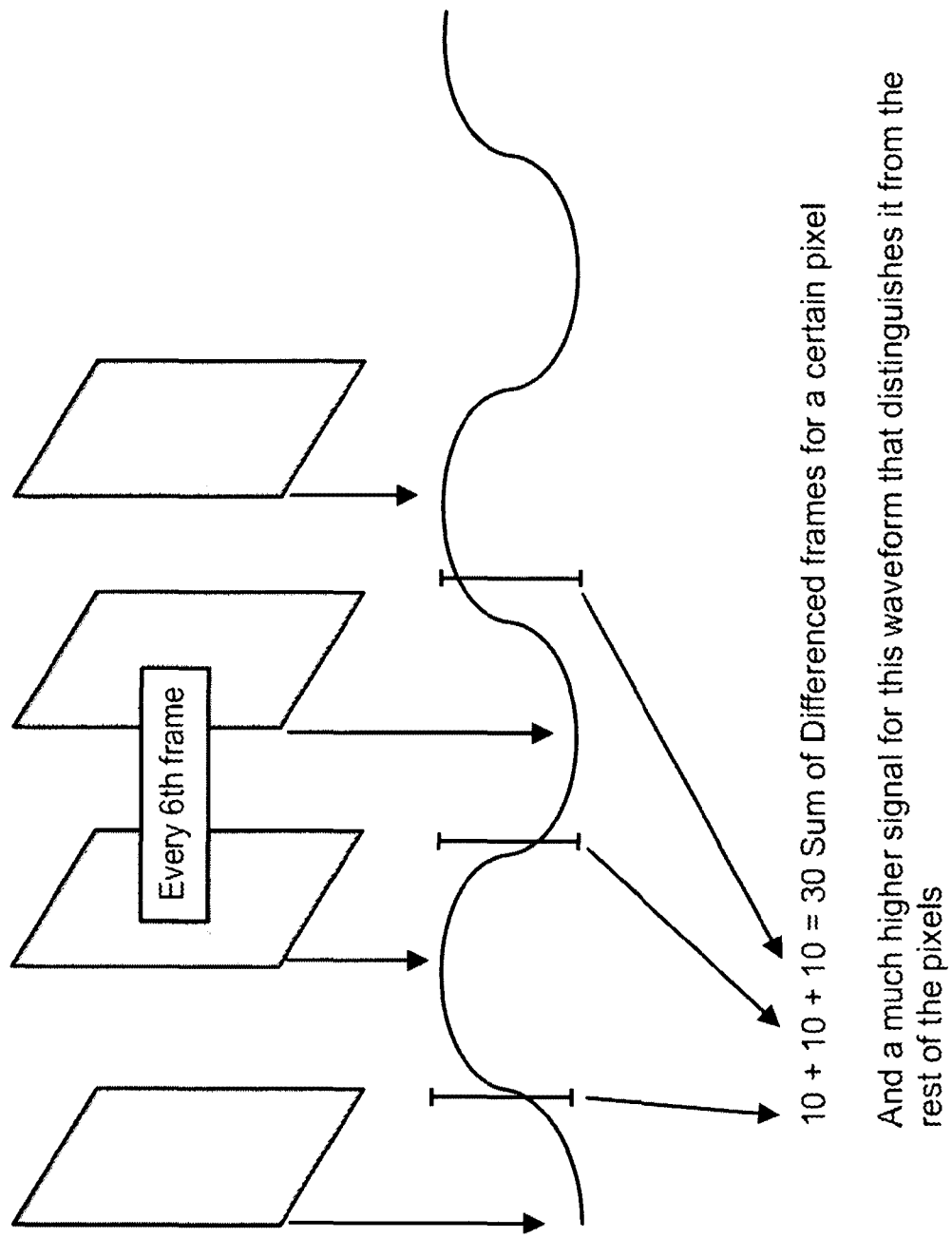
FIG. 3 illustrates the result when the spacing is more nearly optimal, in this case, every 6th frame (N=6).

FIGS. 2 and 3 illustrate how the frame spacing is selected by trying two different spacings and comparing the magnitude of the peak differences. In FIG. 2, every 8th frame is used; this turns out to be a bad or "null" spacing, as the sum of differenced frames for a given pixel is zero. When the spacing is changed to every 6th frame, the sum of differenced frames for a given pixel is 30, indicating a much higher signal for this waveform that distinguishes it from the rest of the pixels.

So therefore, the program would try a multiple of spacings that represent a reasonable range of breathing rates. The program would also offset them or change the phase because the best spacing that perfectly finds the peaks and valleys is also a "null set". Now it knows where to look when this process yields the pixel with the largest sum of the differences. From this pixel it tracks and locates the peaks and valleys of the waveform. Then it will adapt to the individual's waveform with the next calibration.

Example

Figure 4:
FIG. 4 illustrates a summed frame of differenced frames from 20 seconds of video data. Note the method isolated motions associated with the breathing based on the selected frame number separation as indicated by the darkest pixels in the summed frame.

FIG. 4 illustrates the summed frame of differenced frames from 20 seconds of video data collected on a human subject. Note the method has successfully isolated motions associated with the breathing based on the selected frame number separation: here the darkest pixels identify the location of greatest motion found in the chest region from the up/down right/left motion of breathing as seen by the camera. These are the pixels that would then be tracked to determine the breathing waveform. It is important to emphasize that the data presentation in FIG. 4 is not an image per se, but rather simply a graphical display of the pixels (dark) that show the most movement.

Example

An explicit example of the calculations can be shown as follows: Let [1] be the first frame of a video sequence, a 640×480 image, so that [1] is a 640×480 array. Likewise [2] would be the second frame making up a new 640×480 array and [3] would be the third. We would like to sum the difference of every N frames. To ensure the difference is positive we subtract the frames, then square the difference, and then take the square root. Finally we sum all of differenced frames.

For example, if we difference every 8 frames the calculation would be of the form:

$$\sqrt{([1]-[9])^2}+\sqrt{([9]-[17])^2}+\sqrt{([17]-[25])^2}+\sqrt{([25]-[33])^2}=[SUM]$$

Other potential applications and features of the invention include the following:

A user defined setting can be selected (e.g., age) to narrow the window in which rates are expected. Infants, for example, breathe much faster than adults and a low rate is unlikely. It will be appreciated that narrowing the window allows the system to converge more quickly on an optimal frame rate, because this reduces the number of iterations the system has to go through, making it quicker and more accurate as the chance of error would be reduced by eliminating certain frequencies.

Information such as a profile of a particular user's sleeping respiration rate, may be stored and later retrieved so the device has a better range of expected rates to look for a priori. In this case the user selects a profile that the device has gathered over previous uses or parameters that were previously entered.

Sections of the video scene may be selected to narrow the search. For example, if a baby monitor is looking at crib, the user interface might allow the user to draw a box (e.g., on a touch screen) to select only the crib, eliminating the rest of the room. An adult may select his/her bed. Eliminating extraneous parts of the image from consideration will allow the calculations and optimization to proceed more quickly.

A user may draw a line down the middle of the bed designating areas where two people sleep so each person can be tracked individually. Other approaches may not require a user to select or "draw" a region of interest. For example, a vicinity of pixelated focal plane or in a field of view area may be designated by proximity to a bright pixel, portion of an area, or other feature.

One can isolate periodic motion by selecting the range the motion is expected to be in. For example, when studying heart rate or pulse, a reasonable value might be from 60 to 120 bpm.

The system may also be used to determine if something has gone out of range and/or activate an alarm if, for example, no breathing or a heart rate can be found in the expected range. The system may enter a calibration state prior to alarming, to check for a false positive on an alarm. The system may use data in memory, e.g., the last 20 seconds, to instantly analyze this prior data to locate a signal elsewhere in the scene. If no such signal exists, the system may continue with the alarm. If such a signal exists the system may not enter an alarm state and instead indicate that a signal has been found.

The data can be used with a standard peak finding method to determine the max and mins of the waveform.

The system can be used to determine a person's presence, for example the existence of vital signs in a controlled space where no one is supposed to be.

Example

Figure 5:
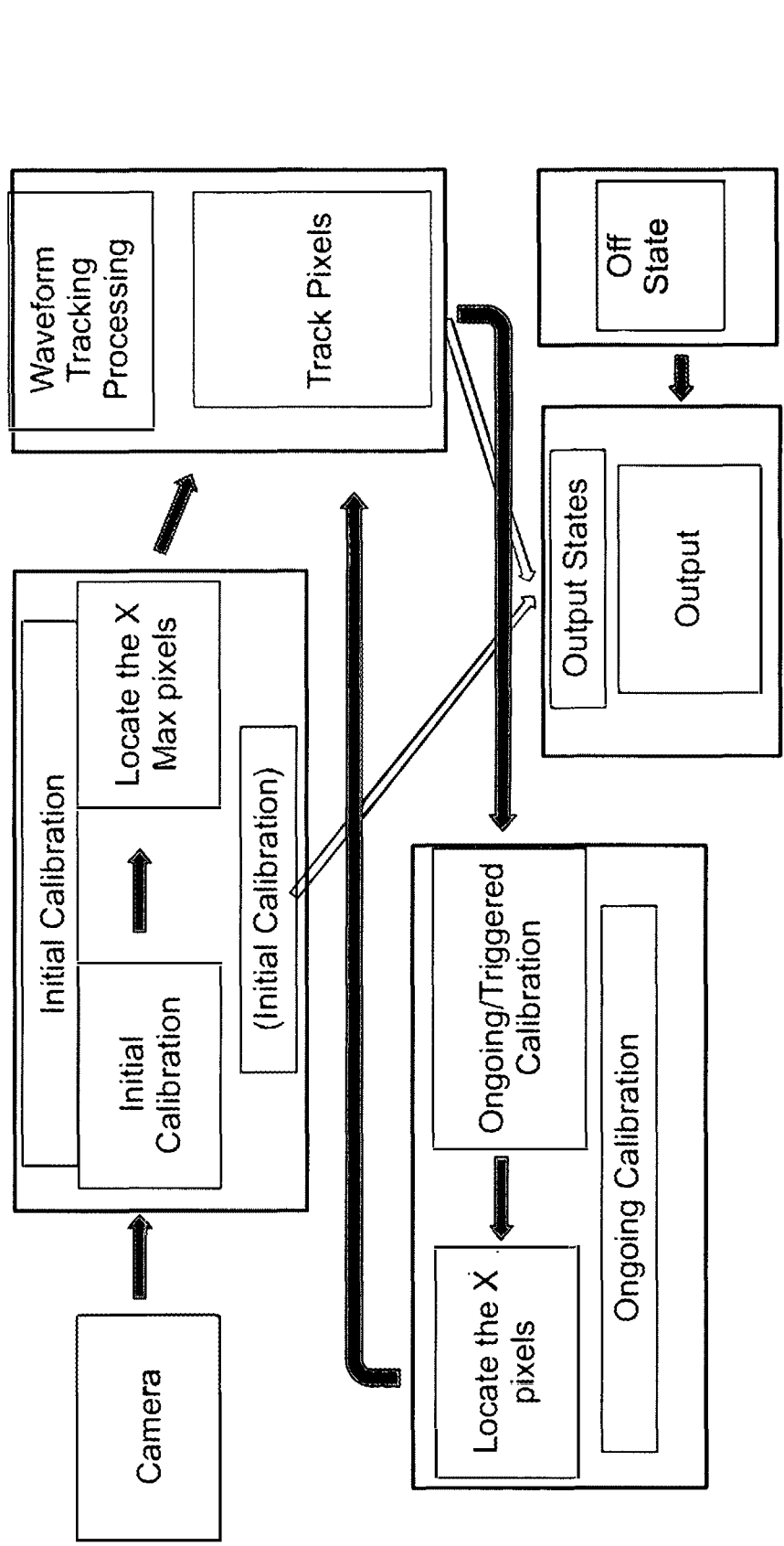
FIG. 5 illustrates a simplified flow chart of the basic camera operation and analysis done in a completely automated process.

FIG. 5 presents a simplified flow chart of the basic camera operation and analysis done in a completely automated process. The input video may be MPEG1 simple profile or MJPEG from, e.g., a USB webcam or similar source. The initial calibration subroutine, typically using 20 s of video, locates the 5 pixels with the greatest values in difference matrix, and establishes State 0, or initial calibration. The waveform tracking and processing subroutine tracks pixels, continuously outputs the last N values of the pixels determined to be the greatest from the difference matrix; processing is done on waveform to determine output states. States 1-3 will be determined in this routine based on processing of the waveforms. An ongoing calibration subroutine is continuously looped; this uses 60 s of frames, summing the difference of frames and locating the five pixels with greatest values in difference matrix. Five output states are continually outputted from the subroutines through a physical channel. Off State condition may be determined by a selected trigger, implemented either in hardware or software.

Example

Calibration Subroutine

A subroutine recalibrates the location to find the best pixels. This consists of going through the process of frame differencing again and locating the 15 highest valued pixels in the summed array. The duration of the calibration can be programmatically controlled as well as the frame numbers to difference as a result they may vary. For example we choose to difference every 4 frames of a 16 fps camera for 40 seconds resulting in 160 differenced frames. Note this is different than the initial calibration since it is limited to 20 seconds.

This recalibration process continually goes on in the background while the waveforms are being outputted from the pixels and the peak finding is performed.

It is important to keep in mind that the mathematical techniques of the present invention derive parametric outputs whether or not an image is ever created or portrayed. Thus, techniques of the present invention may be used with monitors that do not display images, do not recognize objects, and do not have frequent human observation or similar participation. For example, the present invention may output a commonly reported characteristic such as a breathing rate or heart pulse rate or phase or a lag interval or a dimension of a periodically moving object or a period of a motion, or a timing or a motion or other information associated with a periodic motion event without displaying an image thereof. Conversely, in some examples, the user interface may include actual video images, which may be selected to correspond to a particular point in time when an output parameter has a particular value or the waveform displays a particular feature (e.g., an episode when breathing changed or stopped temporarily).

As used herein, the term "video" describes any data set representing a series of digital (i.e., pixelated) images of a scene, taken at fixed time intervals, so that the data represent points in X-Y-t space. The image may represent a pattern of reflected and/or emitted visible light, UV, IR, X-rays, gamma rays, or other electromagnetic radiation detected by a two-dimensional position-sensitive detector. Although certain standard file types have been described in some of the examples, the invention is not limited to any particular frame rate or file format.

It will be further appreciated that the invention is not limited to any particular type of image acquisition hardware; video cameras, webcams, digital cameras integral in cell phones, etc., may also be used to generate the raw data files. The digital imaging device may further include any suitable lenses or other optical components, such as telescopes, microscopes, etc., as are well known in the art. In particular, the invention is well suited for examining periodic movement in small biologic systems, such as heart contractions in an embryo, which could be observed using a video microscope. Adapted to a telescope, the invention could be used, e.g., to study periodic phenomena occurring on the surface of the sun.

Many examples of the present invention are completely general in that they do not require or insist upon a blob that must be identified with an object in the field of view or with a contour segment that must be associated with an object in the field of view.

Techniques of the present invention may be applied to a variety of imaging, including visible imaging, thermal imaging, multispectral imaging, or hyperspectral imaging. In fact these are entirely different and independent media having different sources and different mechanisms and different physical significances. However, the techniques for measuring motion remain the same for any spectral ranges. For example, the use of visible images of an object of interest overlaid (or interleaved, overlapped, interspersed, approximately synchronized, or truly simultaneous) with near or far infrared images may yield two effectively independent views of an object of interest. If reflected visible light reveals a periodic motion which may be associated with a breathing or a pulse or a structural vibration or some other periodic motion, and a thermal image reveals a similar periodic motion location proximate to the visible finding and similar in phase, frequency, or amplitude, or all three, then this improves the likelihood of an accurate result rather than a false positive or false negative finding.

As noted above, the imaging systems may have multiple inputs. These may comprise two visible cameras, an infrared imager and a visible camera, a camera and another input other than an imager such as an ultrasonic sensor or a temperature or a pulse monitor or some other combination of two or more imaging devices.

Figure 6:
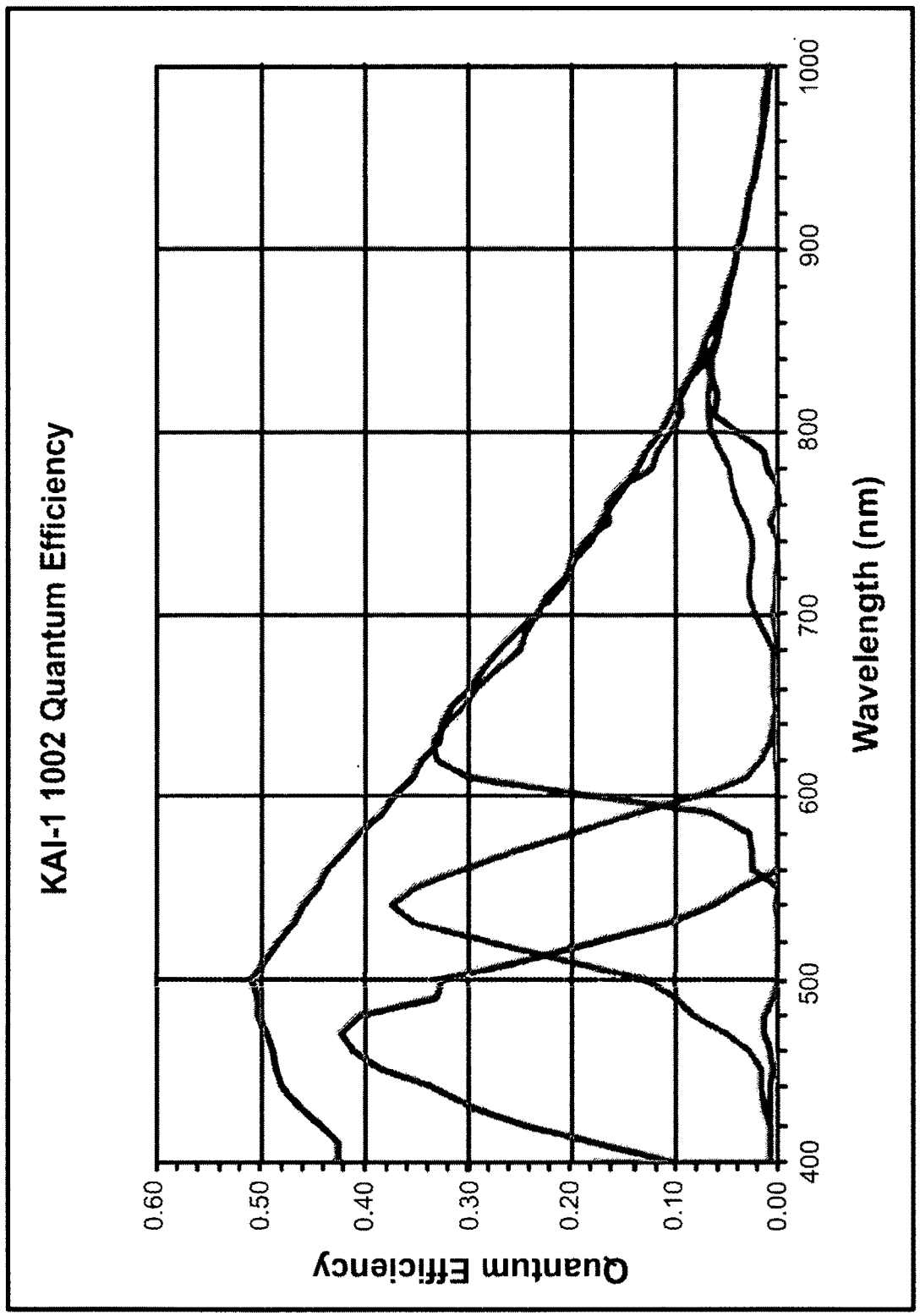
FIG. 6 illustrates the spectral response of a typical color video sensor for the three colors red, blue, and green.

The inventive technique is not limited to a particular wavelength of light. Different colors are represented by different wavelengths of light, e.g. 550 nm is green. Amplitude changes that are detected by this technique can be restricted to a single wavelength of light or represent a summed intensity change over multiple wavelengths. FIG. 6 shows the response of a typical color camera. Each wavelength can be measured independently or together (mono grayscale). The inventive technique may, for example, monitor only the green, blue or red wavelength or monitor the sum of all three.

Electromagnetic Wavelength options. In addition the inventive technique is not just limited to visible wavelength of light, but can be used in the near IR, far IR, or UV. The technique could be extended to any sensor type that can measure changes in light levels over time whether from reflective or emissive sources. Visible light is generally although not always measured as a reflection. Thermal IR light is generally but not always an emission from the surface. The invention works regardless of whether or not the target is reflecting or emitting the light.

Sensor selection. The sensor type can be chosen based on the scene or target. For example, if the scene is completely dark, void of a visible light source, a thermal IR sensor may be used to monitor the changes in light levels. Also if a particular material or substance is the target and light level changes are due to a property of interest on the target another sensor type may be chosen. For example, with gas that absorbs in certain wavelengths, or more generally chemicals, a particular sensor that detects those properties may be chosen. For example, one may be interested in using the technique to find an exhaust or chemical leak in the scene based on light intensity changes from the leak specifically associated with the absorption and/or emission at certain wavelengths. Another example may be blood flow that absorbs in certain colors, and that flow changes or pulsing may be indicated by intensity changes in a certain wavelength of light, then a sensor particularly sensitive to that wavelength of light might be chosen.

Interpreting measurement information. The inventive technique can also be used to garner information about the type of change. A particular change using a thermal sensor would indicate that the temperature is changing, whereas a change in color may indicate the target is changing is absorption or emission properties. A change in amplitude could also be indicative in a change in position or vibration, whereas a change in position of the signal being detected from pixel to pixel in time may give information about displacement.

Comparing multiple measurements. Ratio or comparisons of color changes or amplitudes of certain wavelength can also be used. For example, it may be useful to locate a pixel that changes in intensity from blue to red. This could be indicative of certain properties of interest. An example would be pulsing of blood. The technique could be used to locate a pixel of interest that is indicative of blood flow so that parameter can be tracked. Multiple sensors could be used for this technique or a single sensor with wavelength filters applied (such as a typical color camera). Certain features of interest may be indicated by relationships between multiple sensor sensitivities or wavelength of light.

Redundant and independent inputs. Multiple sensor types or wavelength detections could also provide multiple detections of the same phenomenon increasing the confidence of detection. For example, the light intensity changes due to the periodic motion of the chest from breathing may be detected with a visible or IR camera pointed at the chest while another sensor looks at the intensity change in thermal IR from temperature changes around the nostril indicative of inhalation and exhalation. The technique is then use in both cases to strengthen the detection scheme.

False negative findings. Multiple wavelengths could be used to discern or improve findings which may be false positive and false negative findings and true positive and true negative findings. Intensity shift from multiple wavelength, red, blue, green, IR, etc. could be used in conjunction with each other to improve the signal to noise ratio and also provide multiple independent readings to increase confidence in detection.

Figure 7:
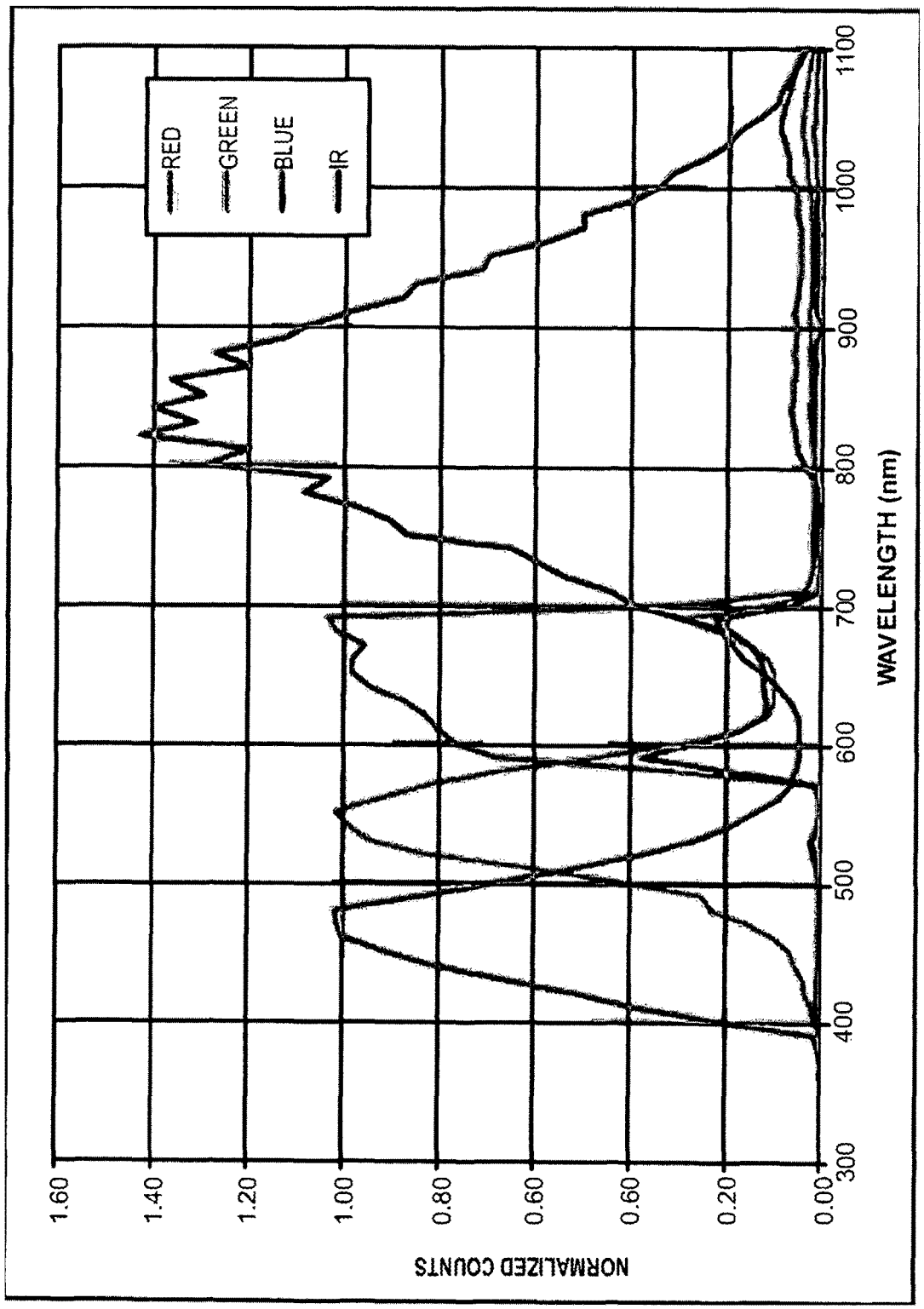
FIG. 7 illustrates typical responses for R, G, B, and IR sensors.
Figure 8:
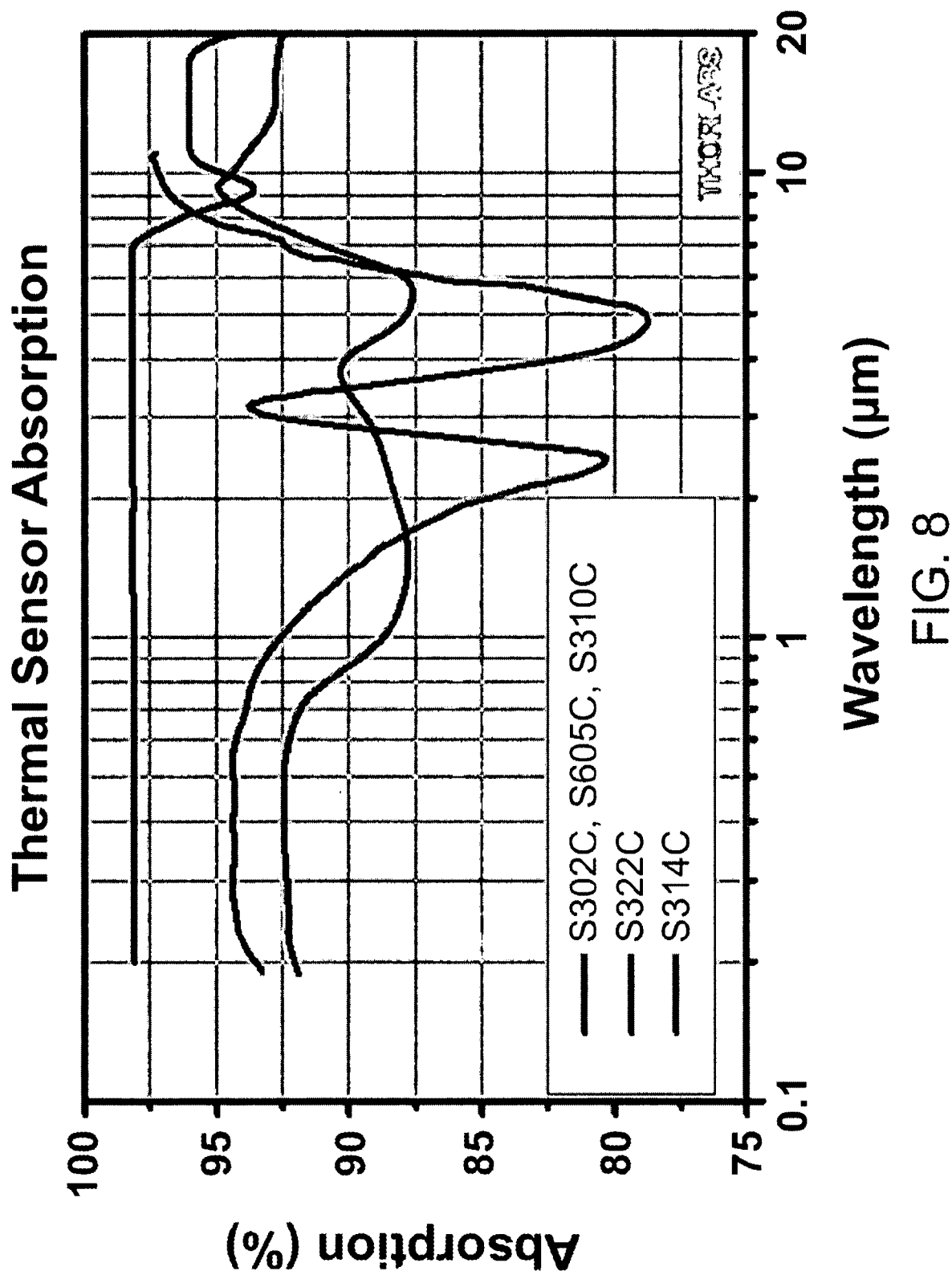
FIG. 8 illustrates the spectral response for several commercial thermal sensors [Thermal Sensors for General Applications—S3xxC Series, Thorlabs, Newton, N.J.].

FIGS. 6 through 8 all show the way in which different sensor types detect different wavelengths of light. Specifically, FIG. 8 shows how a particular wavelength of light is associated with a physical phenomenon, in this case detection of light in different spectral ranges by several different thermal sensors.

Measurement duration. This technique could be used with signals that are repetitive but only over a short time duration. The technique could be applied to shortened windows of time to catch signals that occur only for a set duration. Furthermore it could be used for signals that continually change over time but are ongoing. For example, with a signal that speeds or slows, the time that is used to calibrate or search for a certain intensity change could be shortened to be less than the time change of the signal itself.

Transient event. Additionally there may be irregular or transient events in a periodic signal. This technique could be used in a short enough time window or in a sufficient sequence of waves to extract the location of a periodic signal in the presence of irregular or transient events. FIG. 9 shows an irregular and transient event in an otherwise periodic motion. If the sample window for the technique described here is properly placed the maximum and minimum of the periodic signal can be located. Multiple phase offset would help to address this issue by building up a pixel's sum of differences at a time that the phase offset for a starting point has brought it past the irregular or transient signal occurrence.

Spatial proximity. This technique can find multiple pixels of interest. Spatial relationships between the pixels of interest can further be exploited. For example, if a larger number of pixels of interest were selected and the vast majority of them were found to be in close proximity to each other that could indicate those pixels are related to the same physical phenomenon. Conversely, if they are spread apart and there appears to be no spatial coherence or statistical meaning among the spatial relationship or they are randomly spaced that could indicate they are not related. Furthermore, this technique could also be used to increase confidence in the signal or improve findings which may be false positive and false negative findings and true positive and true negative findings. For example, in a respiration there are likely to be many pixels of interest found near the chest. We could expect a certain percentage to be heavily localized. If this is not the case it may lower our confidence that the respiration was detected. Conversely, if a large number are heavily centralized we may be more confident we have located a physical region undergoing motion from breathing. The confidence may be set by a weighted spatial location mean of the pixels or average separation distance, or standard deviation from the spatially averaged locations of the all pixels of interest.

Breaths per minute. Intensity variations for different pixels of interest can be indicative of certain phenomena of interest. By limiting the temporal separation of which the pixels are differenced and the differenced sum is obtained we can filter for phenomena of interest. For example if we are interested in breathing we limit our frame separation to max and min separation time of waveforms that are indicative of breathing, say 10 to 30 breaths per minute, whereas for the blood pulse we may limit the difference based on max and min separations that fall in the 50 to 100 beats per minute range.

Re-calibration—finding a pixel of interest. It is possible after the technique adapts to find the suitable or best separation to get the largest intensity change based on the differencing of max and min frames, a new search can be performed with that knowledge with tighter constraints to search out specifically that waveform. In that sense it is adaptive after it uses more liberal parameters to find the initial signal. It is possible that a user's information or information on a subject or phenomenon may be stored. The technique can now be used with a priori knowledge of rate, phase etc. to speed up finding the pixels of interest. For example, a user may store his profile, and the technique is then used with knowledge of that user and his typical breathing rate. That way, fewer cycles need to be performed and a tighter constraint can be placed on the technique to find the pixel of interest. For example, only a certain separation of frames are used based on the breathing rate and only the different phases are cycled through.

Visible and infrared photons. Variation in the intensity of pixels may not always result from radiation emitted or reflected by a single object. For example, if something is moving and at a different temperature than the background, that object may move back and forth periodically blocking a small portion of the background. To a thermal sensor, a pixel detecting light in that region will see an increase and decrease in brightness from the object moving back and forth as the object at $T_1$ and then the background at a different temperature $T_2$ are alternately imaged by the pixel.

Multiple cameras. Multiple cameras can be used for multiple detection schemes. They potentially could run at different rates. It is possible to temporally align frames so that certain frames occur at the same time. In this scene the resulting detection of a signal can be temporally aligned as well and correlated. Cameras could potentially be set to image the same field of view. Pixels across multiple cameras or sensors could be correlated so spatial relationships of the pixels in the image of each camera is known.

Other sensors. Other inputs could be correlated to one of more cameras. The detected signal could potentially be correlated to another input signal as well. For example, if a pulse oximeter provides input to the system, the blood pulse and potential respiration timing could be used to validate or increase the confidence of a detected signal determined from a pixel of interest from the technique. Tachometers, accelerometers, and tonometers are all examples of types of sensors that could be used in conjunction with the inventive technique. These input signals could also provide frequencies or phase data to allow the system to use tighter constraints to reduce the number of iterations it goes through or immediately determine the proper phase and or frequency from which to select the differenced frames. These inputs also can be used as triggers for recalibration or other functions.

Single pixel and combination of many pixels Techniques of the present invention may be used with the smallest achievable pixel size or may be used with binned pixels where multiple neighboring pixels are collectively associated (mathematically or statistically) to create a larger virtual pixel. This technique may be done on camera or chip or done afterwards in data processing. Binning may be done horizontally, vertically, or both, and may be done proportionately in both directions or disproportionately. Collective association or binning may potentially leave out or skip individual pixels or groups of pixels. For example, one form of collective association may comprise combining a plurality of bright pixels while ignoring some of all of the pixels not determined to be "bright" or "strong" considering a characteristic of interest such as a selected frequency range or amplitude.

Gaining confidence by eliminating false findings. It may be of interest to increase the confidence of the detection by exploring neighboring pixels. Even if those pixels were not chosen as the ones exhibiting the largest motion they can be explored to determine if at least one or more exhibit the same or strongly correlated waveforms to the pixel of interest. If a physical phenomenon that one is trying to detect is expected to be larger than one pixel, it stands to reason that neighboring pixels undergo similar behavior. Thus it will be clear that this could be used to eliminate false positives in a detection scheme.

Multiplexing. The inventive technique can be applied in a single pixel variant in which an optical element would be used in a multiplex mode where the optical element scans the scene and the transducer samples at each point in the scene. An image or array is created from the scanned data. The sampling/scanning rate is contemplated to be high enough to effectively sample the scene at a fast enough rate to see time-varying signals of interest. Once certain pixels of interest are located, the system would then need only scan those pixels until a recalibration is needed.

Searching a plurality of frequencies. One can compare amplitudes of different subtracted frames separation values, or multiple sums of subtracted frames separation values. For example, comparison can be made between the sum of the subtracted frames for separation X and for separation Y. The frame separations are indicative of frequencies. This comparison will allow one to compare amplitudes of signal changes for different frequencies. Multiple frames separation values that give information about amplitudes of a frequency of the signal can be used to construct a frequency spectrum for a single pixel or multiple pixels.

Arrays representing subtracted frames or sums of subtracted frames at certain frame separation values may be indicative of a frequency. Those arrays may be compared to indicate information about the signals. For example, if two arrays are determined that are indicative of frequency $f_1$ and $f_2$, we may compare those two arrays for determine the spatial distance between the phenomenon that is causing the frequencies. In this case the array may be a spatial image.

The following example will more fully illustrate the inventive method, applied specifically to the case of monitoring respiration.

Example

Initial calibration with a single frame separation value and starting point for frame differencing does not optimize the differenced values specific to the respiration rate or maximum and minimum values in the chest motion. To solve this the system will select multiple frame separation values, all at multiple starting points, to ensure that it finds the optimized signal of interest. A series of waveforms, FIGS. 10A-10D demonstrates this principle.

Figure 10A:
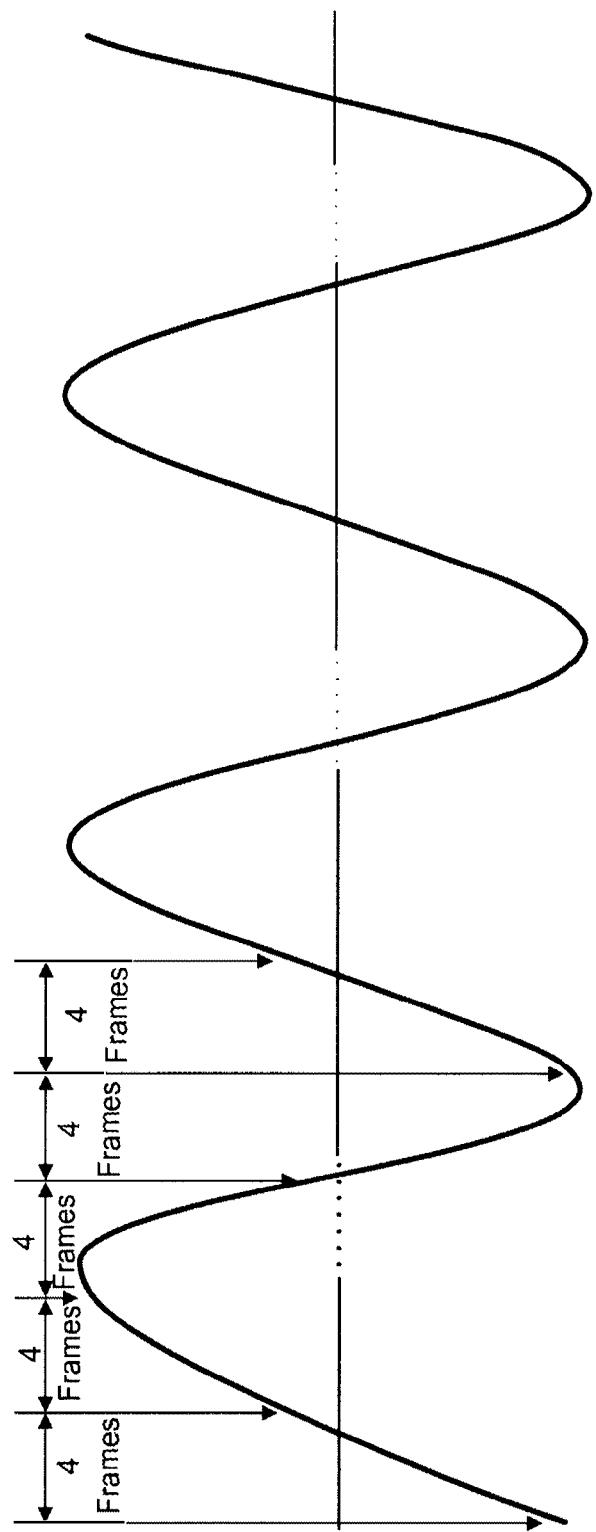

Here we see that at 4 frames of separation, FIG. 10A, the separation does not align with the maximum and minimum peaks in the waveform. Aligning with the maximum and minimum peaks would give the strongest signal indicating that the right separation or rate has been found.

FIG. 10B shows the effect of changing the separation between differenced frames to every 8 frames. One can see that this is better but not quite optimal. Next consider 9 frames, FIG. 10C. To ensure that all possibilities are considered we want the option to select a range for frame separations to subtract as well as the increments in spacing. For example, we subtract from every 2 to 30 frames in increments of 4, or generally we subtract from $N_1$ to $N_n$ in frame separations in increments of $\Delta N$.

In addition to frame separation values, the starting point (referred to as phase in wave mathematics) plays a role in finding the correct frame.

Considering again the case of 9 frames, as shown, it was the correct separation to subtract to find the maximum difference in frames since it aligned with the maximum and minimum in the waveform. Now we choose a new starting point and how it affects the results.

In FIG. 10D, we see that offsetting the starting point to frame number 5 misaligns the 9 frame separation so that it no longer lines up with the maximum and minimum of the waveform. So in addition to doing a multitude of separations, for every separation value we also calculate the difference for multiple offsets. For example, if we difference every 5 frames we do that difference for all offsets from $M_1$ to $M_n$ with an increment of $\Delta M$. An example would be subtracting every 5 frames starting at frame 1 then subtracting every 5 frames starting at frame 2 and so on. Again, in general we want the option to subtract multiple offsets in increments of $\Delta M$ within a range of A to B. For example we may want to increment the offset 5 from 0 to 20. That would mean we do all the ranges of differenced frames starting at frame 0, then do them all again starting at frame 5 and so on.

Once we find the brightest pixels from all the calculations (both all offsets and all frame separations) we now know what pixel to look at, where the waveform starts and what the separation is of the peaks and valleys.

The next calibration we do is adapted to these values and we only calibrate based on those values.

For example, assume that we find that the peaks and valleys separation is every 25 frames and the starting point is 5. Now we know the waveform restarts every 50 frames. So if we recalibrate, it would be at position 55, 105, 155 . . . and so on. This eliminates the need to do all the calibrations above or what we call the initial calibration.

So in terms of the above, the Initial Calibration is the one that does all separations and all starting points. A recalibration (adapted from the initial calibration) uses the known values determined from an initial calibration. All of these operations are done automatically by the processor.

Example

Simple adaptive array comparison example using 3×3 array:

Assume we are using a camera with 9 pixels in a three by three array operating at 10 frames per second.

We believe the signal of interest has a frequency about 0.1 Hz so max and min values will occur at a frequency of 0.2 Hz, meaning max and min values should be about 5 frames apart. We decide to conduct frame differencing tests at 4 frames and 5 frames. Each test will calculate 4 frame differences.

To test the 4 frame possibility, we select frames 1, 5, 9, 13 and 17 for frame differencing. To test the 5 frame possibility we select frames 1, 6, 11, 16 and 21 for frame differencing.

The frames have the following values:

| Frame 1  | 3 | 3 | 5 |                   |   |   |    |
|----------|---|---|---|-------------------|---|---|----|
|          | 3 | 3 | 5 |                   |   |   |    |
|          | 3 | 3 | 5 |                   |   |   |    |
| Frame 5  | 3 | 3 | 0 | Frame Difference 1 | 0 | 0 | 5 |
|          | 3 | 2 | 0 |                   | 0 | 1 | 5 |
|          | 3 | 3 | 0 |                   | 0 | 0 | 5 |
| Frame 9  | 3 | 3 | 5 | Frame Difference 2 | 0 | 0 | 5 |
|          | 3 | 3 | 5 |                   | 0 | 1 | 5 |
|          | 3 | 2 | 5 |                   | 0 | 1 | 5 |
| Frame 13 | 3 | 3 | 0 | Frame Difference 3 | 0 | 0 | 5 |
|          | 3 | 2 | 0 |                   | 0 | 1 | 5 |
|          | 3 | 3 | 0 |                   | 0 | 1 | 5 |
| Frame 17 | 3 | 3 | 5 | Frame Difference 4 | 0 | 0 | 5 |
|          | 3 | 3 | 5 |                   | 0 | 1 | 5 |
|          | 3 | 3 | 5 |                   | 0 | 0 | 5 |
|          |   |   |   | Total Frame Dif.  | 0 | 0 | 20 |
|          |   |   |   |                   | 0 | 4 | 20 |
|          |   |   |   |                   | 0 | 2 | 20 |

In this test, pixels (1,3), (2,3), and (3,3) are selected as the largest pixels, each having a total time frame difference of 20 with a combined total of 20 for the three largest array values

| Frame 1 | 3 | 3 | 4 |                    |   |   |   |
|---------|---|---|---|--------------------|---|---|---|
|         | 3 | 3 | 4 |                    |   |   |   |
|         | 3 | 3 | 4 |                    |   |   |   |
| Frame 6 | 3 | 3 | 0 | Frame Difference 1 | 0 | 0 | 4 |
|         | 3 | 2 | 0 |                    | 0 | 1 | 4 |
|         | 3 | 3 | 0 |                    | 0 | 0 | 0 |

-continued

| | | | | | | | |
|---|---|---|---|---|---|---|---|
| Frame 11 | 3 | 3 | 4 | Frame Difference 2 | 0 | 0 | 4 |
|  | 3 | 3 | 4 |  | 0 | 1 | 4 |
|  | 3 | 2 | 4 |  | 0 | 1 | 0 |
| Frame 16 | 3 | 3 | 0 | Frame Difference 3 | 0 | 0 | 4 |
|  | 3 | 2 | 0 |  | 0 | 1 | 4 |
|  | 3 | 3 | 0 |  | 0 | 1 | 0 |
| Frame 21 | 3 | 3 | 4 | Frame Difference 4 | 0 | 0 | 4 |
|  | 3 | 3 | 4 |  | 0 | 1 | 4 |
|  | 3 | 3 | 4 |  | 0 | 0 | 0 |
|  |  |  |  | Total Frame Dif. | 0 | 0 | 16 |
|  |  |  |  |  | 0 | 4 | 16 |
|  |  |  |  |  | 0 | 2 | 0 |

In this test for five frames, pixels (1,3), (2,2), and (2,3) are selected as having the largest values (16, 4 and 16, respectively) but the total combined value of the three pixels is only 36 as compared to 60 in the test for four time frames. So this test would indicate that a four frame difference is the best time interval and the pixels to be monitored would be (1,3), (2,3), and (3,3). However, similar tests will be run for other phases for both the four and five frame intervals. In the next test, the four frame interval will use frames 2, 6, 10, 14 and 18 and the five frame test will use frames 2, 7, 12, 17 and 22. These further tests are changing the phase of the test. Assuming the next tests produce results that have lower total than 60, the first four frame test will prevail and its "brightest" pixel locations will be chosen for monitoring.

Applicants have also tested the invention, and found that it performs well, even with asymmetric periodic waveforms. Three examples using skewed or asymmetric periodic waveforms: SawtoothRight, SawtoothLeft, and LubdubRight were evaluated as described more fully in Applicant's co-pending application, "Method of adaptive array comparison for the detection and characterization of periodic motion", U.S. Publication No. 2016/0217588. Each of these three waveforms incorporates a skewed 30-frame peak-to-peak periodicity evident. SawtoothRight and SawtoothLeft waveforms have a 2:1 skewed rate of falling compared with rising measurement values. LubdubRight also contains a second peak in each periodic cycle. The inventive method was able to accommodate the features of these waveforms without difficulty.

The user interface may be configured in a wide variety of ways, as described more fully in the following examples.

Example

Figure 11A:
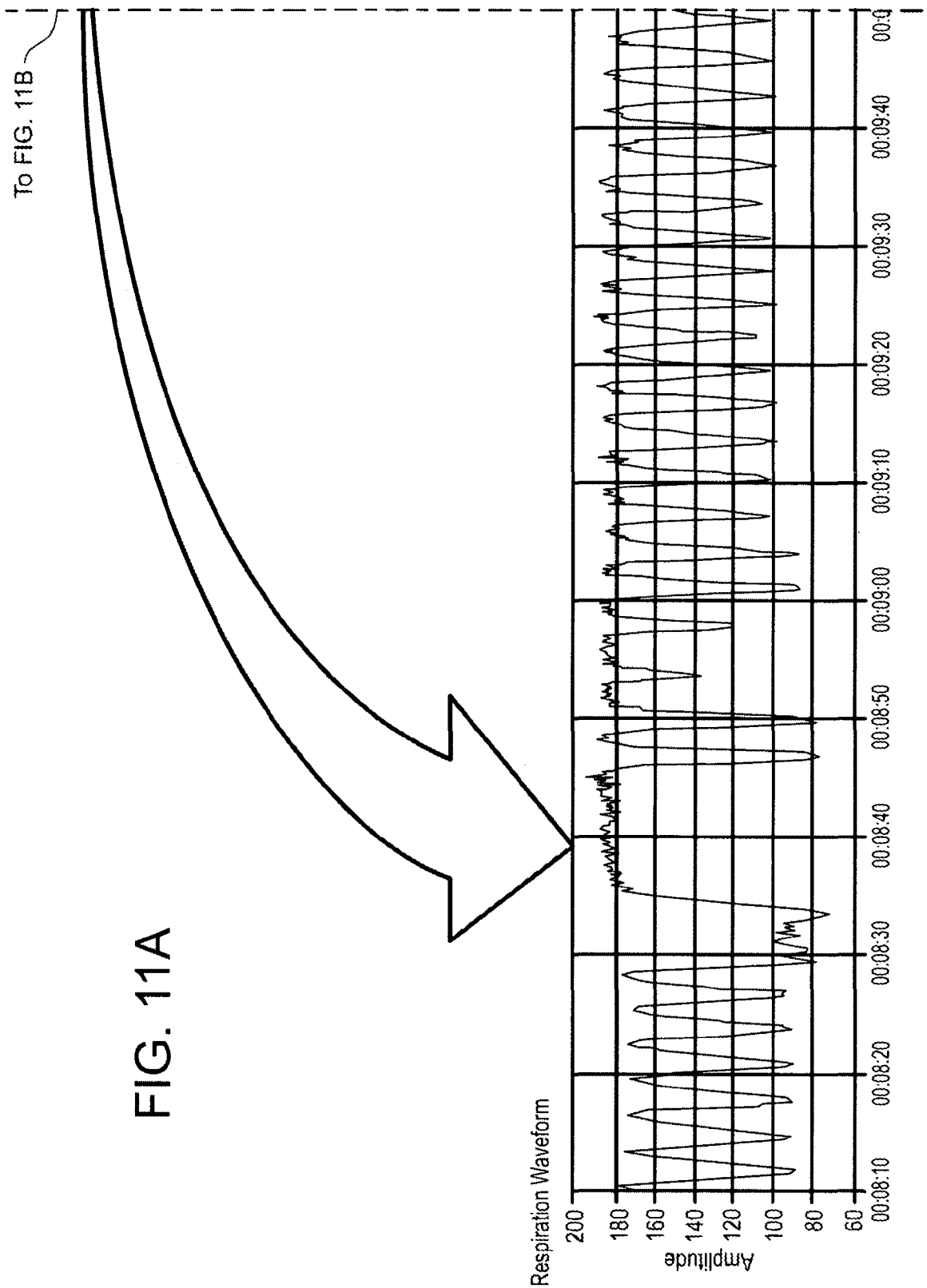
FIGS. 11A and 11B taken together illustrate the ability of a user to rewind the acquired data files (indicated schematically by the large arrow) to return to a point in time at which an event occurred (here, an irregularity in the respiration waveform).
Figure 11B:
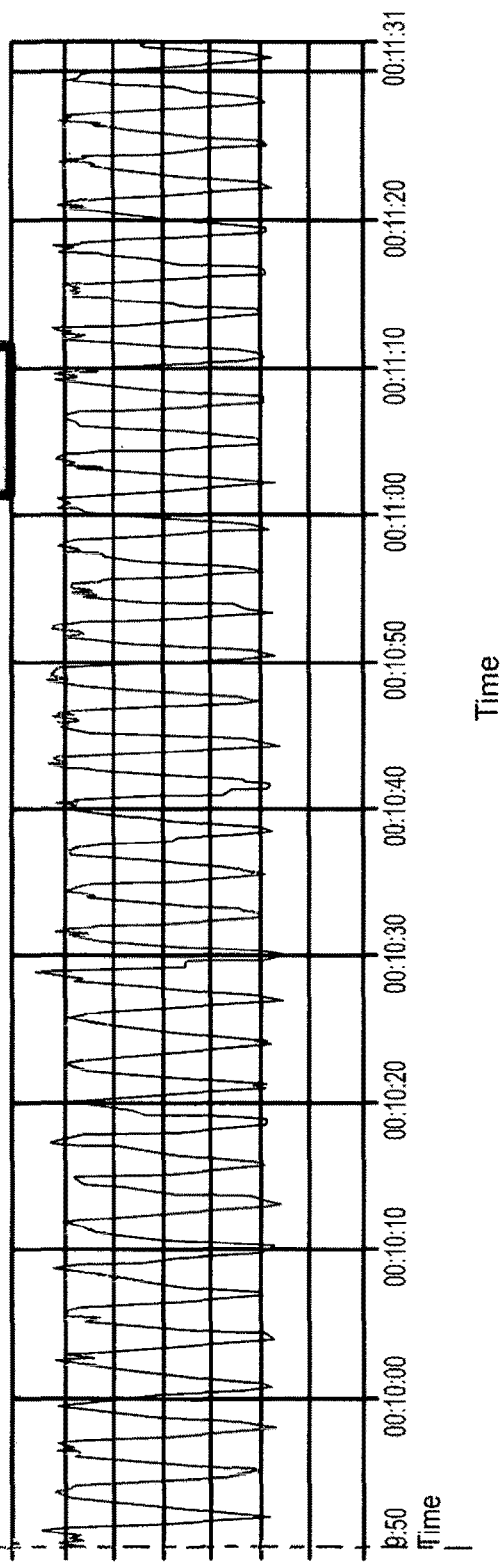

Because the data may be stored with the raw video on a common time basis, if an alarms sounds and everything appears to be normal, the user may simply rewind the video to review more closely what caused the irregularity, as shown conceptually by the heavy arrow spanning from FIG. 11B to FIG. 11A. The information, in this case, might include the video, respiration waveform, and a sleep quality index. So the user might press a button that rewinds the waveforms and video or goes back a preselected amount of time or to a specific preselected time and plays back the waveform and video side by side to show what triggered an event or an alarm condition, thus providing a more complete understanding of the event.

Example

Figure 9A:
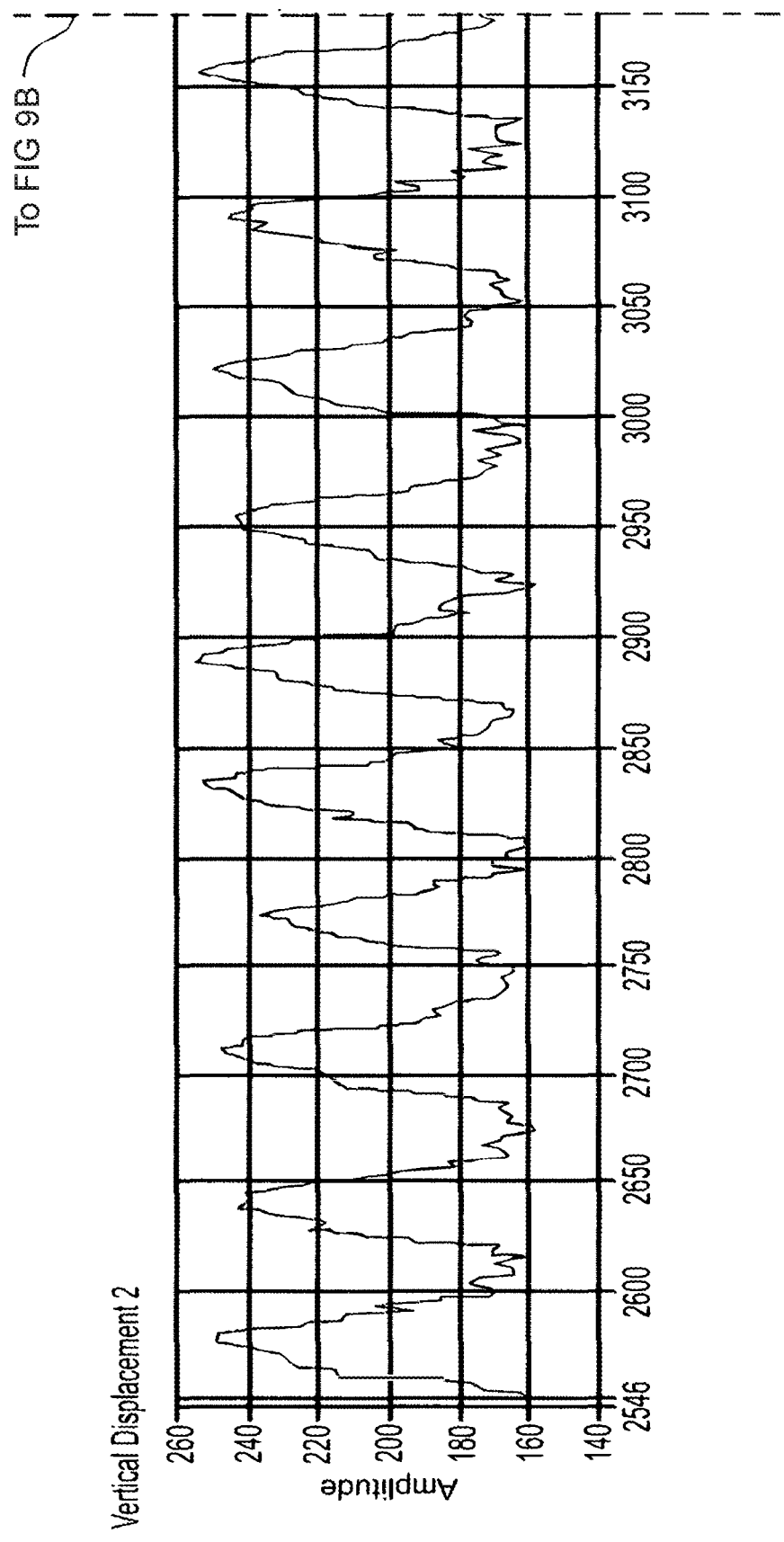
FIGS. 9A and 9B illustrate one regular or healthy respiration waveform.
Figure 9B:
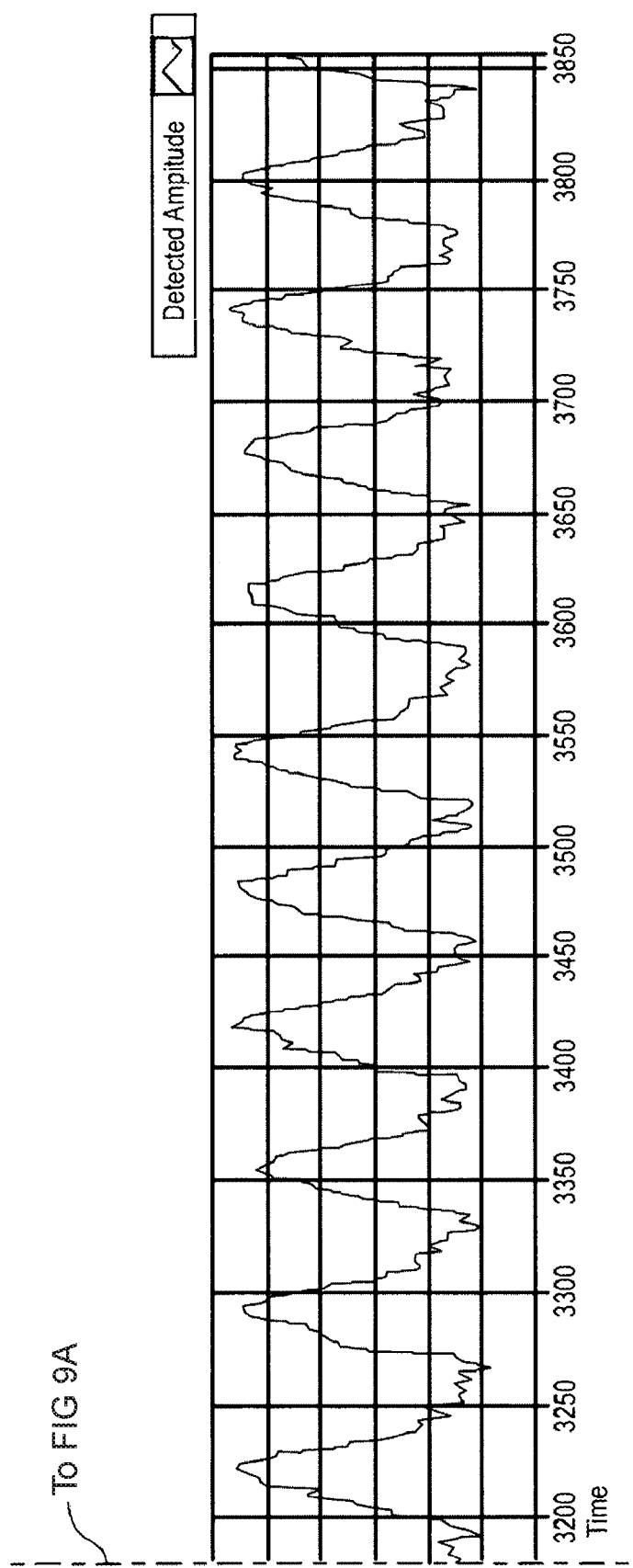
Figure 9D:
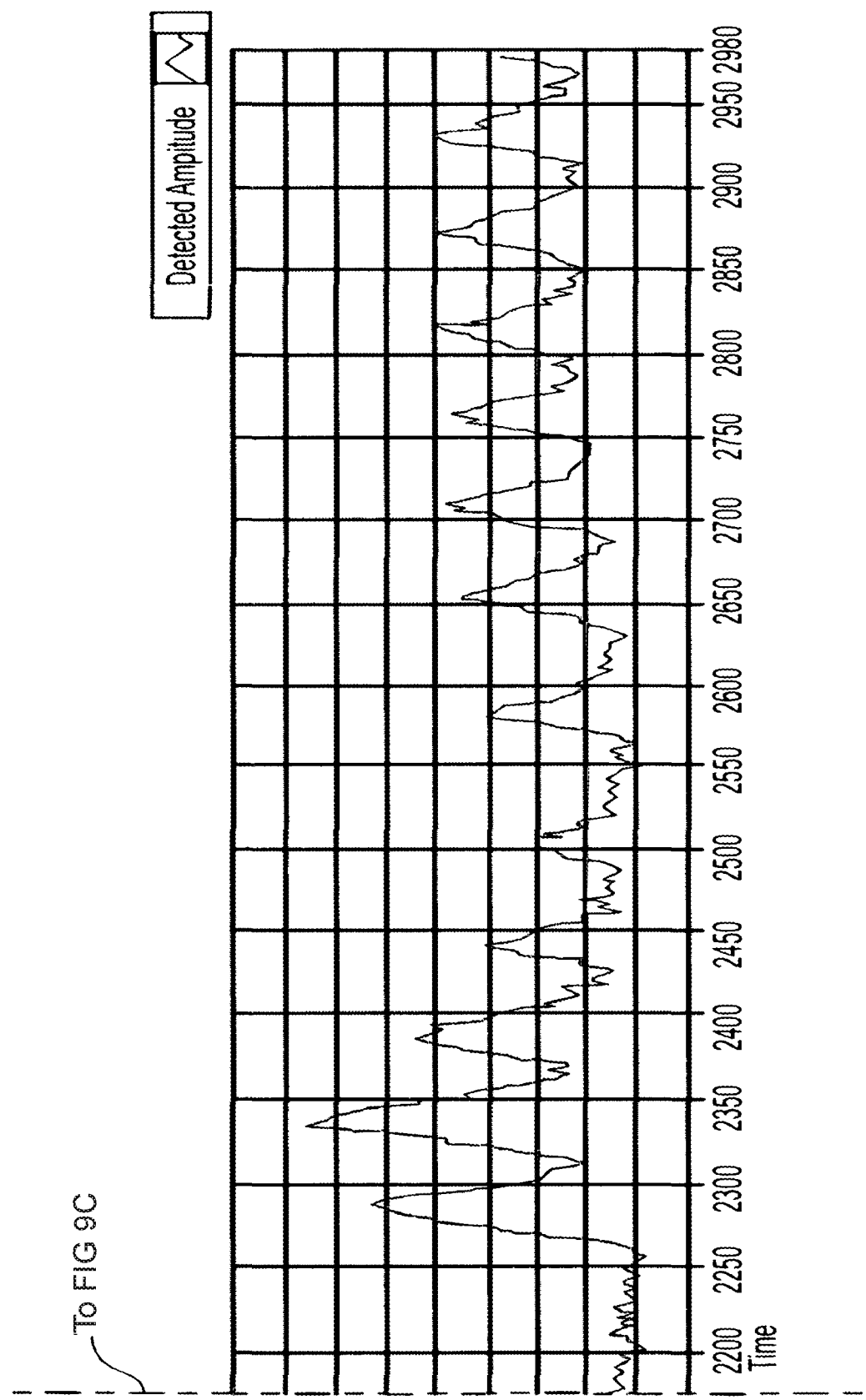

Using Waveform Signatures to Detect Events. FIGS. 9A and 9B, which appear on two drawing sheets but consist of one wave, show a healthy waveform and FIGS. 9C and 9D show an irregular one. 9C and 9D also appear on two drawing sheets but consist of one wave. An event is clearly seen in the middle of the irregular one. Here this event will be categorized, stored, indexed and/or reported and may contribute to the sleep quality index.

Templates may be prepared to help the user correlate an event to some known conditions. For example a set of templates may exist including a healthy waveform and each breath is correlated against that template to define what feature it best represents. That information would then be used to contribute to the sleep quality index. The information may also be uploaded to a central database and/or provided to a health care professional. The information may also be included in a report. Exemplary templates may include, but are not limited to, an obstructive event, an apnea event, a central apnea event, an obstructive apnea event, a healthy waveform, or a snoring waveform. Templates can be correlated to the waveform in real time or in post processing to find the best suitable match and characterize waveforms according to the highest correlated match. These values are then stored and may be supplied as characterized events. The totals might be indicated after a night's sleep.

Events may be indexed and a single frame or video clip may be extracted that corresponded to the same time. Those compilations may be stored. One index may be targeted in particular, for example, obstructive apnea events or sleeplessness characterized by motion. The user may review those events to determine his sleeping position to determine if he sleeps better in a particular position. The position may be automatically determined from the video and events may be correlated to a sleep position automatically to determine better or worse sleep positions.

Events may be correlated with timing through the day/night and the same procedure as described above would allow the user to determine if particular times of day/night are correlated with better or worse quality of sleep.

Example

FIG. 12A shows a video image of an infant and FIG. 12B shows a waveform where the waveform was measured from the video data and shown in real-time. This can be displayed on the user interface. A waveform can be derived from the video wherein the waveform is plotted in real-time with the corresponding video. FIG. 12A shows a frame taken from a video of an infant who has been diagnosed with central and obstructive sleep apnea. The child stopped breathing for about 20 seconds and this can be seen in the flat lining of the waveform shown in FIG. 12B.

It will be appreciated that the user interface may take a variety of forms, and in particular, the invention may be implemented in a mobile application, so that, for example, a parent can view the data acquired by a small digital camera placed in the child's room.

Example

Figure 13:
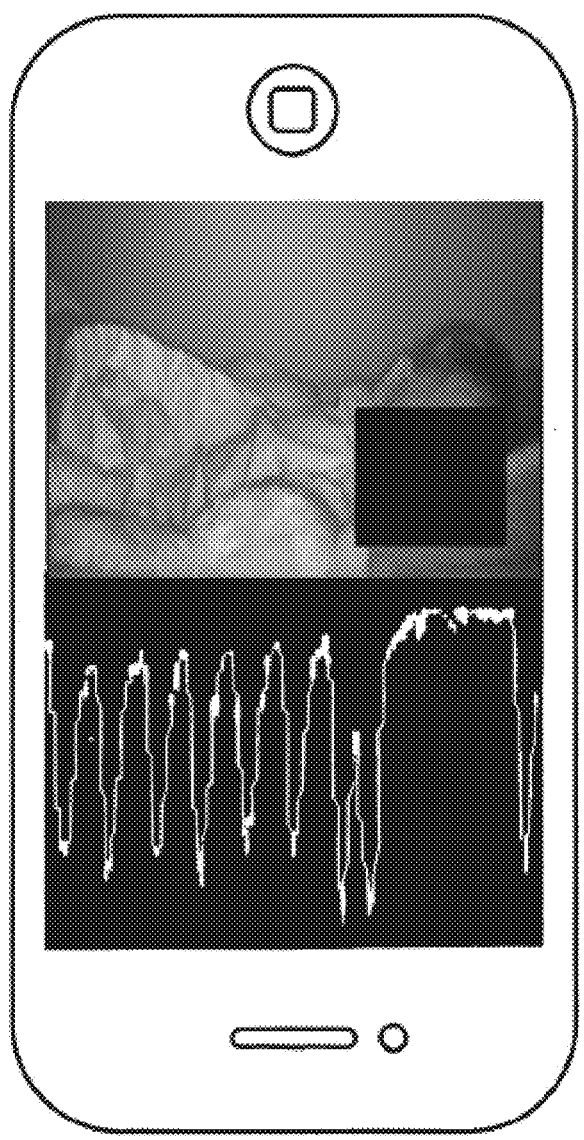
FIG. 13 illustrates an example of a user interface implemented for mobile devices.

FIG. 13 shows an image of a potential graphical user interface (GUI) showing the respiration waveform and video in real-time from a camera where the respiration waveform is derived from the video. The interface allows the user to view the data using a smart phone.

The camera does not have to be placed right next to the child in the playpen, crib, carrier, etc. Applicant has discovered through experimentation that the inventive process is sufficiently robust that reliable data can be collected from a sleeping child in a random position on the bed and surrounded by various objects including blankets, stuffed toys, and the like. Similarly, data can be collected from an adult sleeping normally. This emphasizes an important advantage of the invention, viz., that the measurement itself is not invasive or disruptive. In traditional sleep monitoring methods, the patient wears a wiring harness and other contraptions, which clearly introduce a completely unnatural aspect to the test.

Example

Figure 14A:
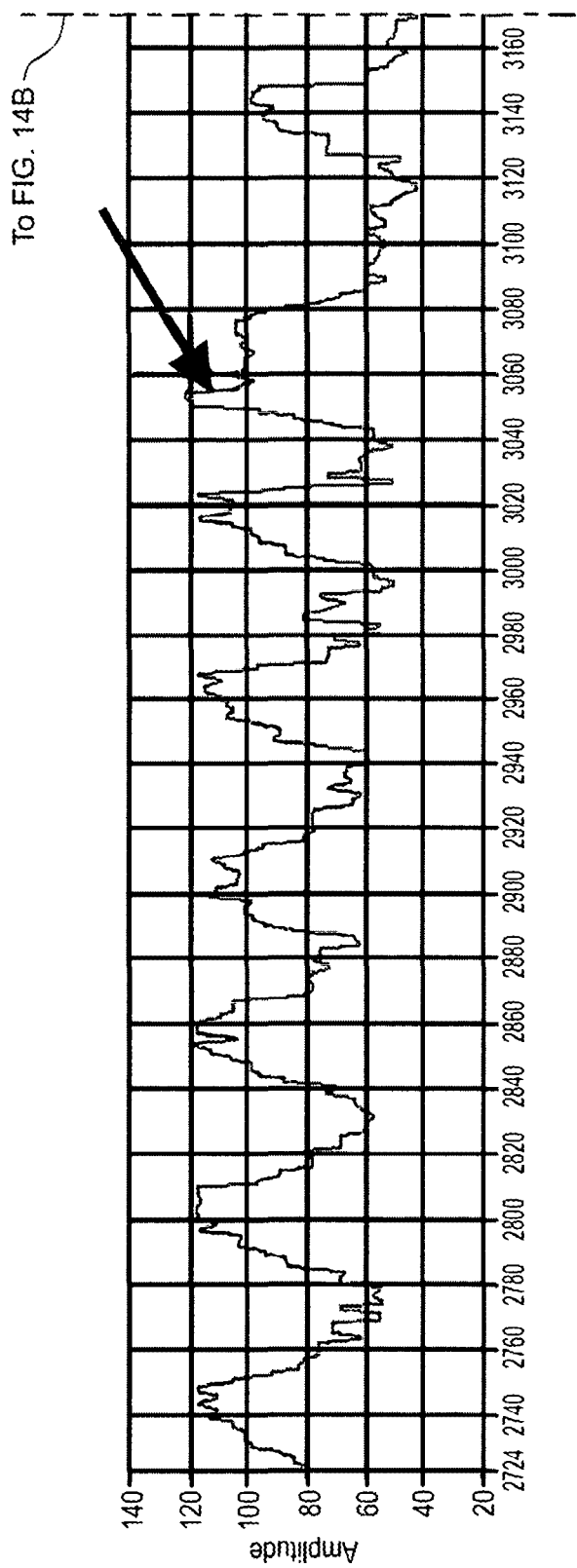
FIGS. 14A and 14B taken together illustrate a respiration waveform containing patterns that may be associated with particular pathologies (arrow).
Figure 14B:
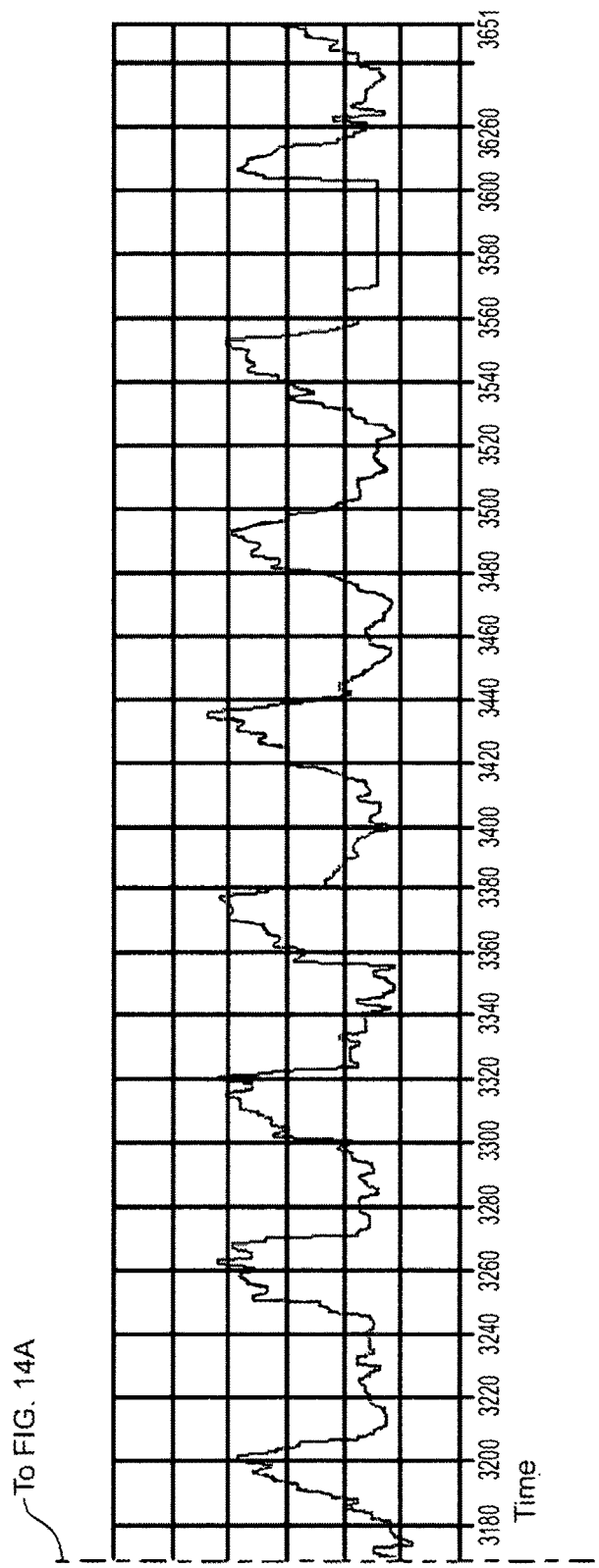

Signatures in the waveform can be correlated to particular conditions, such as normal breathing, flow limitation, obstructive hypopnea, and obstructive apnea. FIGS. 14A and 14B show a waveform where individual features are seen that can be correlated to physical parameters and conditions. The arrow indicates an obstructive apnea event. (It is well known that obstructive events are often identified by the plateau seen at the indicated peak in the waveform of FIG. 14A.)

Example

Ability to Track More than One Waveform. Conventional standoff and contact methods cannot test more than one person at a time. The ability to do so would be valuable for parent/child co-sleeping as well as for instances where two children are sleeping in the same room.

Applicants have experimentally demonstrated that a mother and child co-sleeping as shown in FIG. 15A were simultaneously detected, with the invention capturing dual waveforms from the same video image and displaying both waveforms simultaneously, with the mother's (Individual 1) waveform shown in FIG. 15B and the child's (Individual 2) waveform shown in FIG. 15C.

It will be clear to the skilled artisan that the invention can be used in a hospital room to monitor two individuals simultaneously in separate beds, in a neonatal unit to monitor multiple infants in different cribs, or to monitor to adults sitting in different chairs. The information may be uploaded to the cloud or to a server for continuous monitoring or, for example, to a health care professional or nurse's station.

Example

Figure 16:
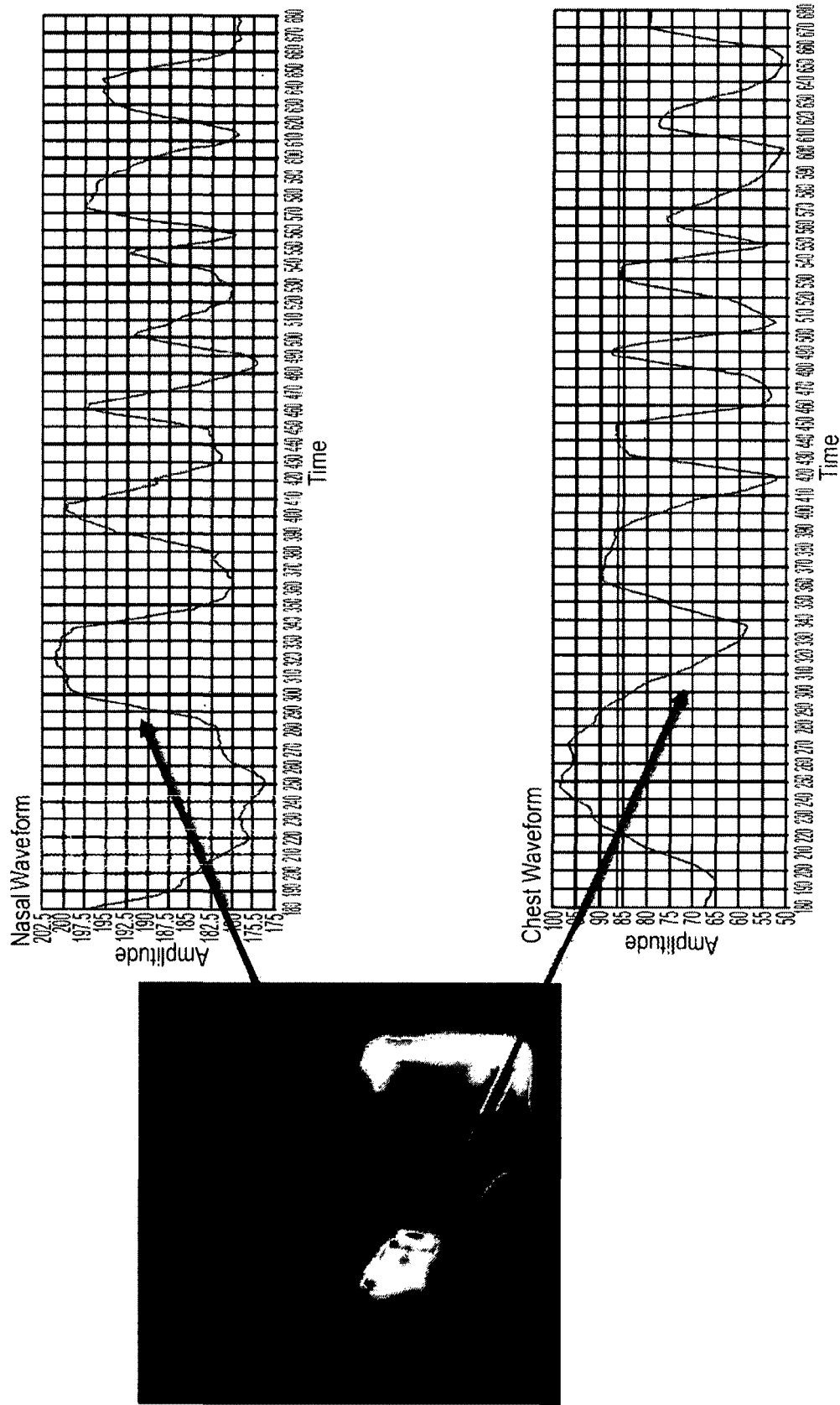
FIG. 16 illustrates the simultaneous analysis of breathing via IR (left part of image and upper data trace) and visible chest displacement (right part of image and lower data trace).

Measuring Two Channels of Respiration. Two respiratory channels can be measured by combining the inventive method (respiratory effort and inspiration/exhalation) with observations from an infrared camera. Thermal imaging along with this method can determine flow by measuring the temperature change around the nasal area and face. Normal light camera along with this method can determine respiratory effort by measuring displacement around the chest area. This eliminates all contact devices necessary in an in home sleep study except the wireless pulse oximeter on the patient's finger. This allows for two required independent methods of respiratory function measurement and can be used in apnea detection. FIG. 16 shows both measurements at the nose (upper curve) and chest (lower curve) being simultaneously captured through the combination of optical and with thermal imagery.

Inhalation and exhalation from the nose can be measured using the invention. Respiratory Effort from the chest can be measured at the same time to determine whether a patient's breath is being blocked or the brain is not sending the signal to breathe (Obstructive vs. Central Apnea).

Thermal measurements or thermometer measurements can be correlated with the sleep index, restlessness or other index indicating sleep quality, and the ambient temperature of the room can be adjusted to a temperature that is better suited for sleep.

The device may track sleep quality and determine better temperatures for sleep. The invention can be integrated or communicate with a thermostat or other external device to record and store ambient temperatures and thermostat settings. The system may correlate that data with sleep information including, but not limited to, sleep position, sleep quality index, respiration rate, thermal reading of body temperature, and ambient sleep environment. The system could use that information to learn optimal sleep situations including temperature and temperature cycles to automatically adjust the thermostat to maximize sleep quality, comfort, and sleep conditions. The user may indicate the aggressiveness of the sleep-to-thermostat control. The user may have various zones within the home controlled separately based on different sleep monitors. The user may program ranges within which the sleep device may adjust the thermostat.

Example

Figure 17:
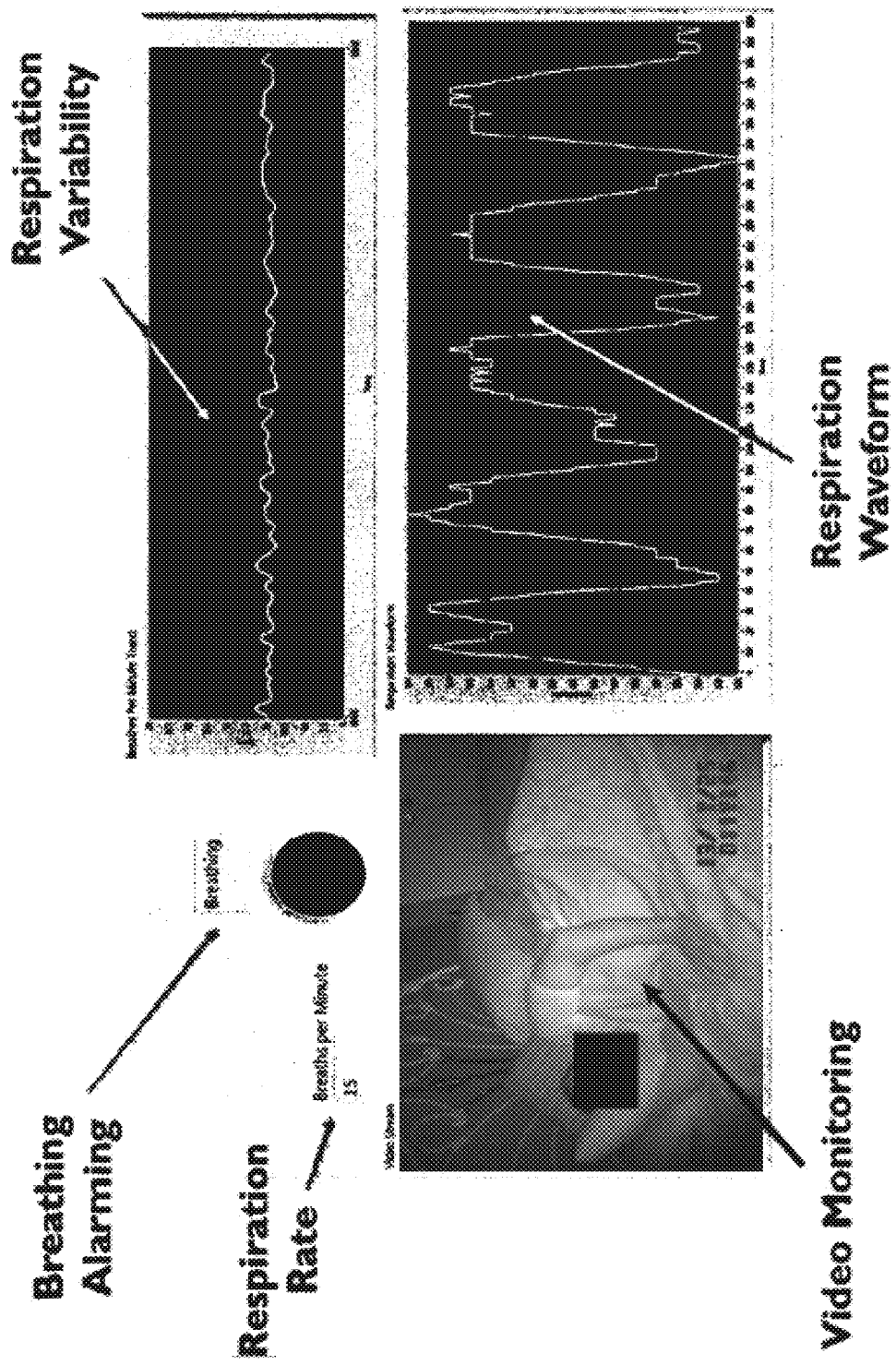
FIG. 17 illustrates one example of a user interface displaying video image(s) along with data derived by the inventive methods.

FIG. 17 shows an example of a user interface that displays multiple elements being measured from the respiration data, along with the video image of the patient. These elements can be combined to form a sleep quality index that is determined and reported to the user compiled from data over a preselected amount of time, for example a night or week. Individual components may be weighted and contribute to the total sleep quality index. Again, the interface may be adapted to a mobile device, smart phone, laptop, or a central location such as a nurse's station.

Example

Figure 18A:
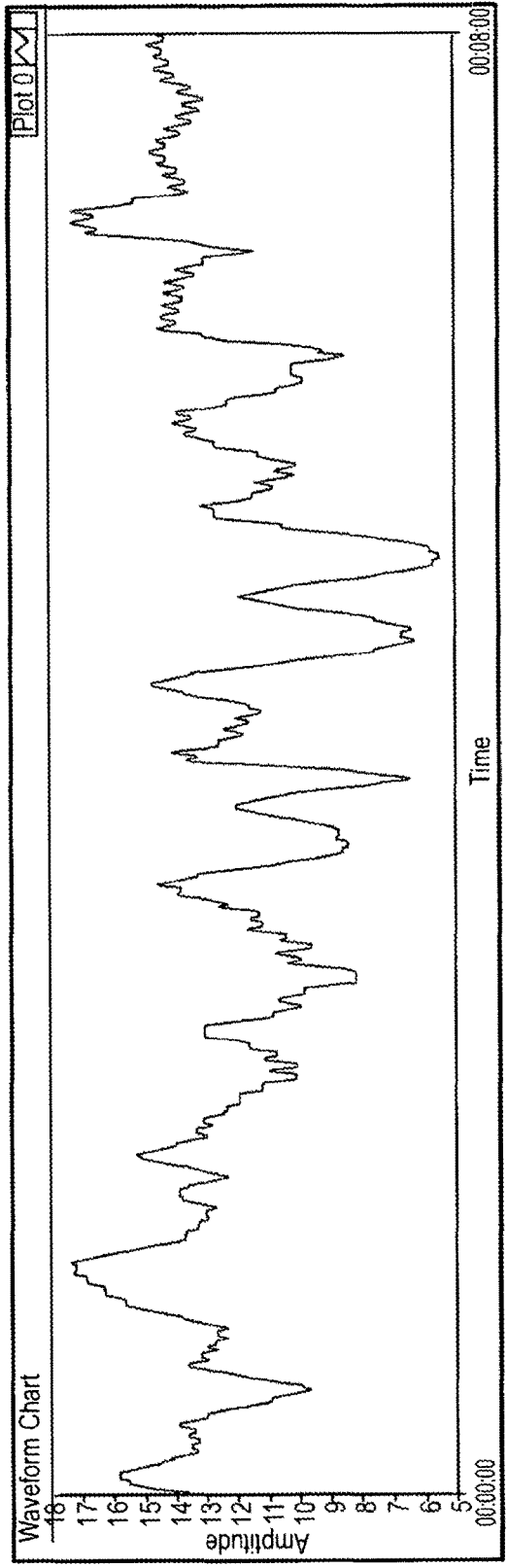
FIG. 18A illustrates the sleeping respiration rates of a male.
Figure 18B:
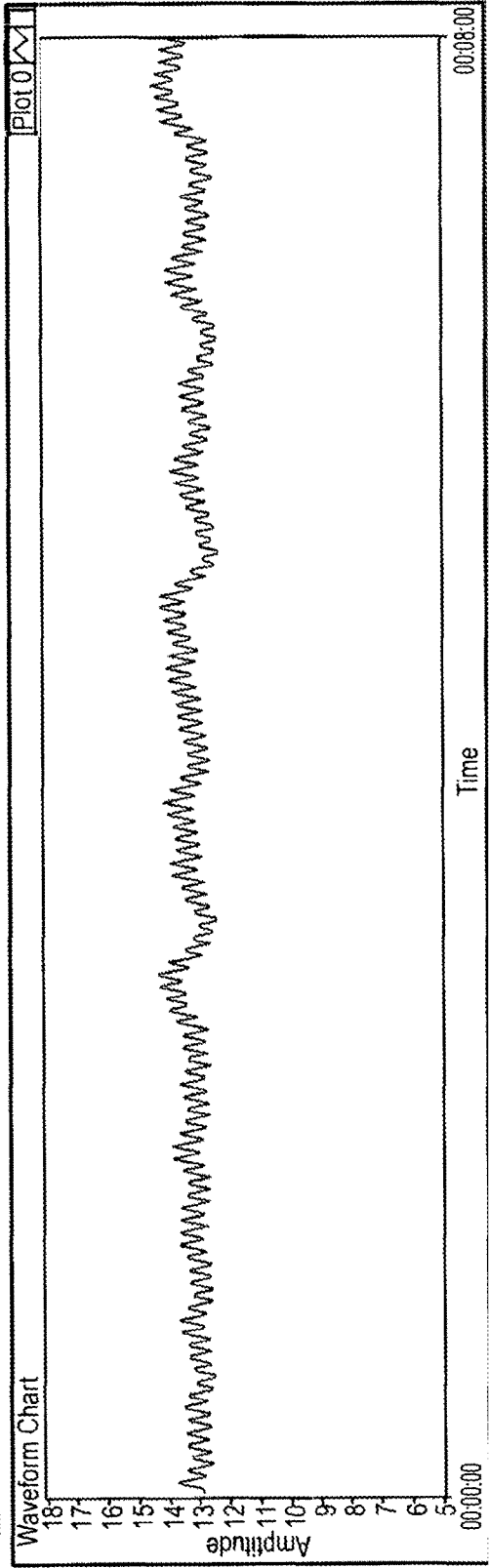
FIG. 18B illustrates the different sleeping respiration rate of a male of the same age.

FIGS. 18A and 18B show how this method can track respiration variability, the frequency of breaths over time, to indicate differences in respiration, by comparing the different sleeping respiration patterns for a male shown in FIG. 18A and another male of the same age in FIG. 18B. This pattern can be tracked, stored, displayed, reported to the user, reported to a healthcare provider, or integrated into an electronic health records system.

Many additional applications may be contemplated for the invention. For example, using a thermal camera, the invention may be adapted to allow a user to hold the camera up to himself and get temperature, respiration, heart rate and respiratory effort readings.

Using a normal cellphone or mobile device, the application could produce respiration rate and respiratory effort results. Applicants have demonstrated that currently-available mobile devices have sufficient computing power to do this. The invention currently runs successfully on an ARM11 Raspberry Pi board which is slower than the current iPhones and likely the iPhone 5s too. An early prototype ran successfully on the iPhone 5s using its internal camera.

The application could run for an extended time period or be used for a number of consumer reasons, e.g.: sick family member (replacing the thermometer with richer data); tool for patient assessment in the doctor's office; as an exercise monitor; and as a monitor for other chronic or acute health conditions.

It will be appreciated that the invention may also be used in a veterinary setting, e.g., to monitor the condition of a pet under observation in a kennel. The non-contacting nature of the invention makes it especially helpful in the case of large or dangerous animals, e.g., monitoring the condition of a pregnant elephant, farm animal, lion, etc., and monitoring the health of newly-born young in the presence of a protective mother.

Although many of the Examples disclosed herein relate particularly to cardiovascular parameters (pulse, breathing, etc.), it will be appreciated that other vital signs may be of interest. These might include physical movements associated with tremors, tics, spasms, seizures, etc. For example, the invention may be used to study hand tremors in order to quantify the onset, progress, and treatment of Parkinson's disease. Quantifying eye movements may provide information on various pathologies, drug use, state of intoxication, etc.

Example

Psychogenic nonepileptic seizures (PNES) are paroxysmal episodes that somewhat resemble epileptic seizures but are of psychological origin (emotional or stress-related). They seem to arise spontaneously at widely-spaced and random intervals. PNES episodes (or pseudoseizures) are difficult to distinguish from true epileptic seizures, but may be differentiated by their periodicity, with true seizures being much more periodic and pseudoseizures being more aperiodic. The difficulty in either case is that the events occur randomly and often days apart, so they are difficult to observe in a clinical setting.

Using the invention, a camera could be positioned in the patient's room and operate unattended for an extended period. Then, when motions other than those associated with breathing are detected, the data can be collected and quantified to better characterize the behavior as a true seizure versus a PNES episode.

Although in many cases, the video file to be analyzed contains images of the patient, it will be appreciated that the invention may equally well be used in other novel ways to obtain information, particularly regarding tremors. In that mode, instead of directly imaging the patient, the patient (user) may simply hold a small video camera (e.g., webcam or smart phone) and collect a video stream focused on some fixed object. The apparent motion of the fixed object will therefore be directly related to the movement of the user's hand, as described in the following Example.

Example

For characterizing tremors of the hand, the user might focus the camera on a predetermined object, e.g., a card having fiducial marks thereon, and collect a video file of, say, 20 seconds. The images of the card would be simple to analyze, and if the sampling procedure were standardized, data would be very easy to track over time. So the health care provider might instruct the patient as follows:
 1. Place the card on the wall
 2. Place the camera 2 feet from the card
 3. Hold the camera in your hand with your elbow on the table
 4. Collect video for 20 s.

The analysis and archiving of the resulting data may be done in many convenient ways. For example, the user might log into the provider's web site, hold a webcam, and upload or stream the video in real time. The provider's computer would analyze the file, compare to archived data, determine trends and advise the patient if some action is needed. Alternatively, the user might have an app residing in a smart phone, allowing the video clip to be collected and sent to the provider via email or other protocol. Thirdly, the app might do all of the necessary computation on-board and display the results for comparison to archived results, so that the user may see a trend or change and decide if a visit to the doctor is called for.

The provider might maintain a larger database of many patients, along with key elements of their medical histories, allowing important correlations to be drawn regarding medications and other clinical factors that would not be apparent from one patient's history. This type of information could, for instance, be very helpful in clinical trials of new treatments.

The foregoing discussion and examples were generally directed to the case of individual monitoring of a patient in a home or clinical setting. However, Applicants also contemplate a number of applications in the areas of law enforcement, public health, and national security. Examples of these applications include the following.

Example

Respiration is known to be affected by the state of stress, and indeed respiration is a key element in a conventional lie detector. It will be appreciated, therefore, that the invention may be used, overtly or covertly, to assess the truthfulness of a person who is under interrogation. It may likewise find use in detecting individuals who might be under stress because they are about to carry out a terrorist attack. Here an advantage is the ability of the invention to isolate the respiration of one person in a group, as discussed above for the case of several individuals sleeping in the same room or bed.

Example

The invention can also be used in public health emergencies, such as an outbreak of influenza, SARS, etc., where the ability to detect sick individuals in public places, such as airports, becomes critical. Combining respiratory data with IR images provides a particularly powerful tool for identifying a person who is in distress and is likely contagious. Using video imagery for a determination of respiration, allows the observation to be made through a transparent and/or semitransparent barrier in the event a quarantine is necessary for the individual(s).

Example

On the battlefield, inaccessible soldiers can be monitored from a distance for respiration rate, an important vital sign. The information can be used to determine vital signs, whether there is life and death situation, assess the condition of multiple soldiers, and be used to determine the urgency for need of care. In extreme situations, it can be used to determine if a soldier is wounded or dead, which will influence whether other troops should place themselves in harm's way to attempt an immediate rescue.

Some specific implementations of the invention for respiration monitoring include:

Noncontact Baby Monitor: A monitor comprising a standard video camera and/or thermal camera that incorporates the inventive methods and software inside the system or through the display interface, will determine respiratory effort, respiration rate, and whether or not the baby is breathing. The system will alarm if there is no breathing detected. It will be displayed as a video and a waveform with a light that indicates breathing or not breathing and a sleep quality index based on restlessness and breaths taken per minute.

In-Hospital Respiration Monitor: A monitor comprising a standard video camera and/or thermal camera that incorporates the inventive methods and software inside the system or through the display interface, will determine respiratory effort, respiration rate, and whether or not the patient is breathing. The system will typically face the patient's bed and will interface with a physician or nurses' station. The system will send alerts if a patient's condition is deteriorating and will alarm if the patient is not breathing.

Neonatal Respiratory Monitor: A monitor comprising a standard video camera that incorporates the inventive methods and software inside the system or through the display interface, will determine respiratory effort, respiration rate, and whether each neonate is breathing or not. The system will typically have a camera situated where it can take video data of all patients in the NICU. The system will section off the cribs and create individual zones that monitor each patient. The system is capable of monitoring and tracking several patients in one setting for continuous condition assessment by both hospital staff and parents.

In Lab Sleep Study: A monitor comprising a standard video camera and/or thermal camera technology and using the inventive methods to extrapolate an analog chest respiratory effort signal, may send that signal into the current software used by lab technicians to monitor patients overnight in a conventional sleep lab.

At Home Sleep Study: A monitor comprising a standard video camera alone or in combination with an infrared camera or infrared camera alone, will determine respiratory effort, respiration rate, and other breathing parameters to diagnose sleep apnea (Central and Obstructive) through the use of the inventive methods and software.

Vital Signs Checkpoint Tool: A tool comprising a combined infrared and/or standard video camera along with the inventive methods and software will determine respiratory effort, breaths per minute, temperature, and heart rate. The system may be a device that can be affixed to a cell phone and will measure all points with a simple point and click method. This would enable nurses in acute care setting such as the emergency room or a physician's office to take vitals without patient contact, thereby reducing the risk of spreading disease. A similar system would enable individuals to be monitored at travel checkpoints and to be tested for illness, stress, or other abnormal condition.

Using the inventive methods, simultaneous pulse measurements can be made at various locations on the body, e.g., the neck, wrist or ankle. The pulse transit time may be calculated based on the difference in time between pulse arrivals. Using the methods describe previously of finding peaks and valleys one can calculate the phase difference and thus the $\Delta T$ for the pulse transit. This may be done with one or more cameras. Alternatively, when two waveforms at different locations are located, the system may determine peak locations in time at multiple points in the time waveform and by comparison automatically return the pulse transit time.

Vital signs may be distinguished from other signals, i.e., eliminate false positives by various means. Multiple pixels can simultaneously find for example a pulse waveform. The locations of these pixels can help determine if it is a true signal. Pulse measurements would be expected to be localized for example from the motion on the wrist. One may calculate the density of the distribution of pixels exhibiting the expected behavior of a pulse. If the pixels are distributed correctly e.g. high density or specific locations in the image, then the system may report a positive detection, alternatively it reports a negative detection. The same may be true of respiration signals. If the pixel imaging size is known, for example a pixel images 1.0 mm on the target, the system could use that information to determine a relative size of the area in which it expects to see a concentration of signal. This could act as a spatial filter to eliminate false positives. An example would be to set a limit, perhaps the chest size, to see a concentration of respiration signal within the expected chest size, or a small coin-size area for a pulse measurement.

The same method described above could be used to distinguished two people or multiple vital signs. Concentrated areas of positive detection could indicate one person or vital whereas a second concentrated area may indicate another person's vital. For example, two concentrated areas detecting breathing that are spaced apart could distinguish two different people.

As noted earlier, in some cases it is contemplated that the invention may be employed in areas where multiple individuals might be present, e.g., parent and child, or several infants in a nursery. Applicants have found that various means of creating or identifying perimeters may be used to enhance the detection and isolation of a person or waveform of interest.

Multiple Region Perimeter Tracking and Monitoring

A perimeter-tracking approach may be used to prevent an unknown factor from entering the crib or monitoring space of the individual or simply a general area. This can also be used for objects exiting the area. The user will be able to create a perimeter (via a user interface) around the area that he/she wants to monitor and does not want any intrusion into.

In the case of biological monitoring this will prevent situations like an animal entering the monitoring area and the monitor picking up the animal's respiration instead of the human being monitored. When something new appears in the chosen frame either by crossing the perimeter or by appearing spontaneously an alarm will sound or alert issued to notify the user that the monitoring area has been compromised.

Multiple methods of motion detection can be used in the perimeters. For example, a technique such as adaptive array comparison can be used to see if changes have occurred around the perimeter from one frame of the video to the next.

Another technique may be comparison of frame intensity values in the area of interest. Regions can be selected and those regions summed for a total intensity level. If that intensity level changes frame to frame by a certain threshold, motion is determined to have occurred.

Blob comparison may also be used for motion detection.

Single pixel edge motion may be used. It will be possible to determine the perimeter with great accuracy based on movement of an edge of a single pixel or virtual pixel, which will allow for a much greater degree of accuracy compared to using conventional blob techniques. The area being selected does not have to be a series of large boxes as in current technology but instead can be any sort of perimeter that the user chooses to select. This could offer the ability to use a very narrow single pixel perimeter or single virtual pixel comprised of multiple pixels.

Feature tracking may be used by locating features in the perimeter and tracking their location in the perimeter. If their centroid location changes then motion is detected. Correlation of a selected number of pixels with a feature in them can be correlated to sub-regions in successive frames to determine if the highest correlation of the original set of pixels is correlated more highly to another location other than the original location.

Example

Figure 19:
FIG. 19 illustrates a scene in which the perimeter of a user-defined monitored region is shown as a heavy white line.
Figure 20:
FIG. 20 indicates several possible examples of sources of movement (arrows) that might be detected by traverse of the defined boundary.

FIG. 19 shows a picture of a child sleeping with the interior region of interest containing the child inside the monitored region or perimeter. FIG. 20 is another example of a monitored region interior to the white line. Several examples are shown demonstrating events where an object exterior to the region of interest might enter the perimeter region and cross into the interior area of interest. Examples include a hat falling (lower arrow), a poster falling (upper arrow), or a pet entering the bed (not shown).

It will be understood that there are several factors that could create a false positive reading of respiration, including but not limited to outside factors such as wind from the outdoors or a fan, vibration from a device in the room, movement of a curtain or other object in the room, an animal in the field of view, or latent movement from someone near the subject. To help factor out these false positive readings Applicants contemplate the use of various techniques to isolate targets of interest.

Example

Figure 21:
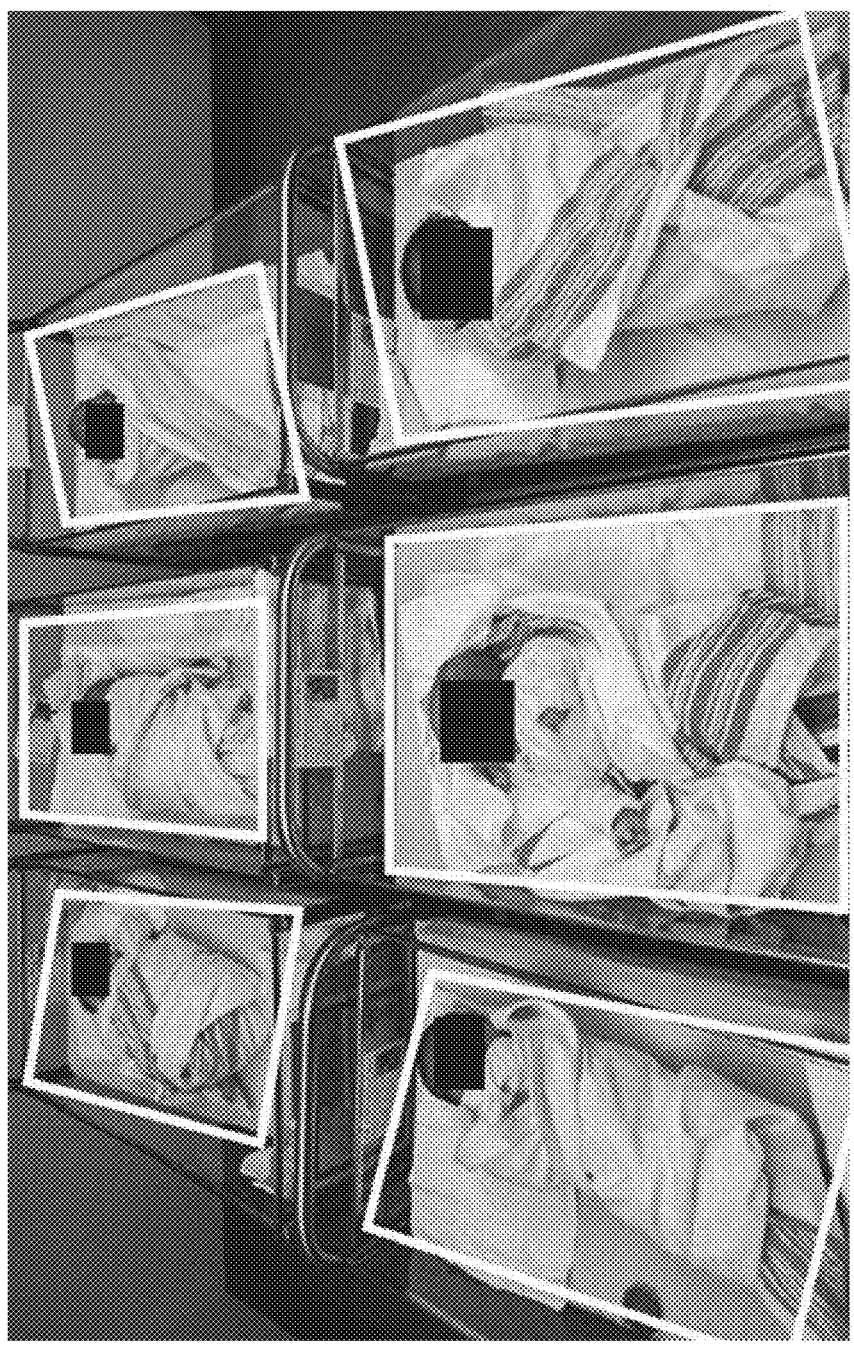
FIG. 21 shows the placement of boundaries (heavy white lines) to define multiple monitored regions in a single video image of a neonatal care environment.

The invention may be installed and used in conditions where there are multiple regions to isolate, such as a shared hospital room or neonatal unit. Each area can have separate perimeter monitoring as shown by the heavy white boundary lines in FIG. 21.

Figure 22:
FIG. 22 shows some possible sources of repetitive movements in a room in which two individuals are sleeping and are to be simultaneously monitored for respiration.

Isolation of Frequency:

Applicants have also recognized that the invention may further use frequency isolation and a learning algorithm to learn the individual's respiration rate and distinguish it from outside factors that could produce a vibration or movement in the field of view of the camera, as shown generally in FIG. 22. This will help distinguish movements in the field of view, indicated schematically by arrows, (such as from a floor fan 221 or wind blowing a curtain 222) from movements associated with respiration. This will also help to distinguish between the respiration rate of an animal and a human. It can help isolate an adult's respiration from a child's respiration to ensure that both individuals are being monitoring during a co-sleeping situation.

In a co-sleeping situation a perimeter may be drawn around two individuals in the same bed. A perimeter breach and detection of motion in each individual's perimeters may indicate that the signal being detected from each person's interior region of interest has been compromised and corrupted by the signals the other person introduces. Further, by isolating the location of the breach, information can be gained that will allow the system to automatically, or with user intervention, redraw the perimeters to once again isolate signals being generated by each individual. An example would be if one person rolls towards the other person and breaches his/her perimeter. The location of where they rolled can be determined through motion detection and the perimeters redrawn, shifted to account for the fact that the person is moved thus once again isolating each individual within their respective new perimeters.

Example

Figure 23:
FIG. 23 shows a simple rectangular boundary substantially defining the area inside an infant's crib.
Figure 24:
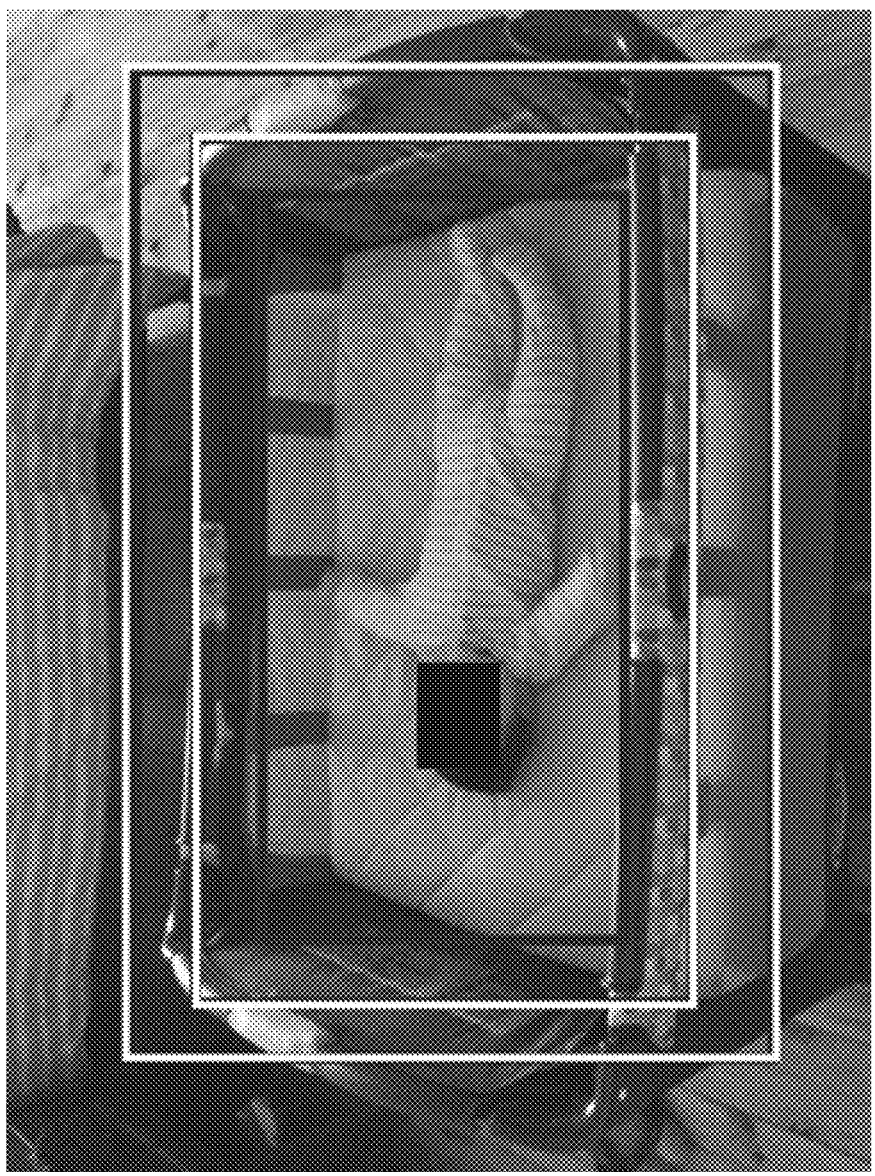
FIG. 24 shows the use of two perimeters surrounding an interior region of interest.

The area monitored can comprise a simple rectangle or more complex shape that is user defined, as shown schematically in FIG. 23. There may be two areas or perimeters of finite width that are monitored as shown in FIG. 24. Monitoring of motion of these two perimeters can be done with timestamps or in the temporal domain to determine the order in which motion is detected. This would allow for the direction of the motion to be determined to ascertain whether an object is entering or exiting the area of interest interior to both perimeters. Decisions can be made based on this information. For example, if an object is exiting the area no action may be taken; however, action may be taken if an object is entering the area of interest inside the perimeters.

Motion may be allowed inside the area of interest without alerting or affecting the monitoring of the perimeters. This would allow for an object to freely move within the area of interest, for example a baby playing or a baby sleeping and breathing, but still allow for monitoring of the perimeters.

Example

Figure 25:
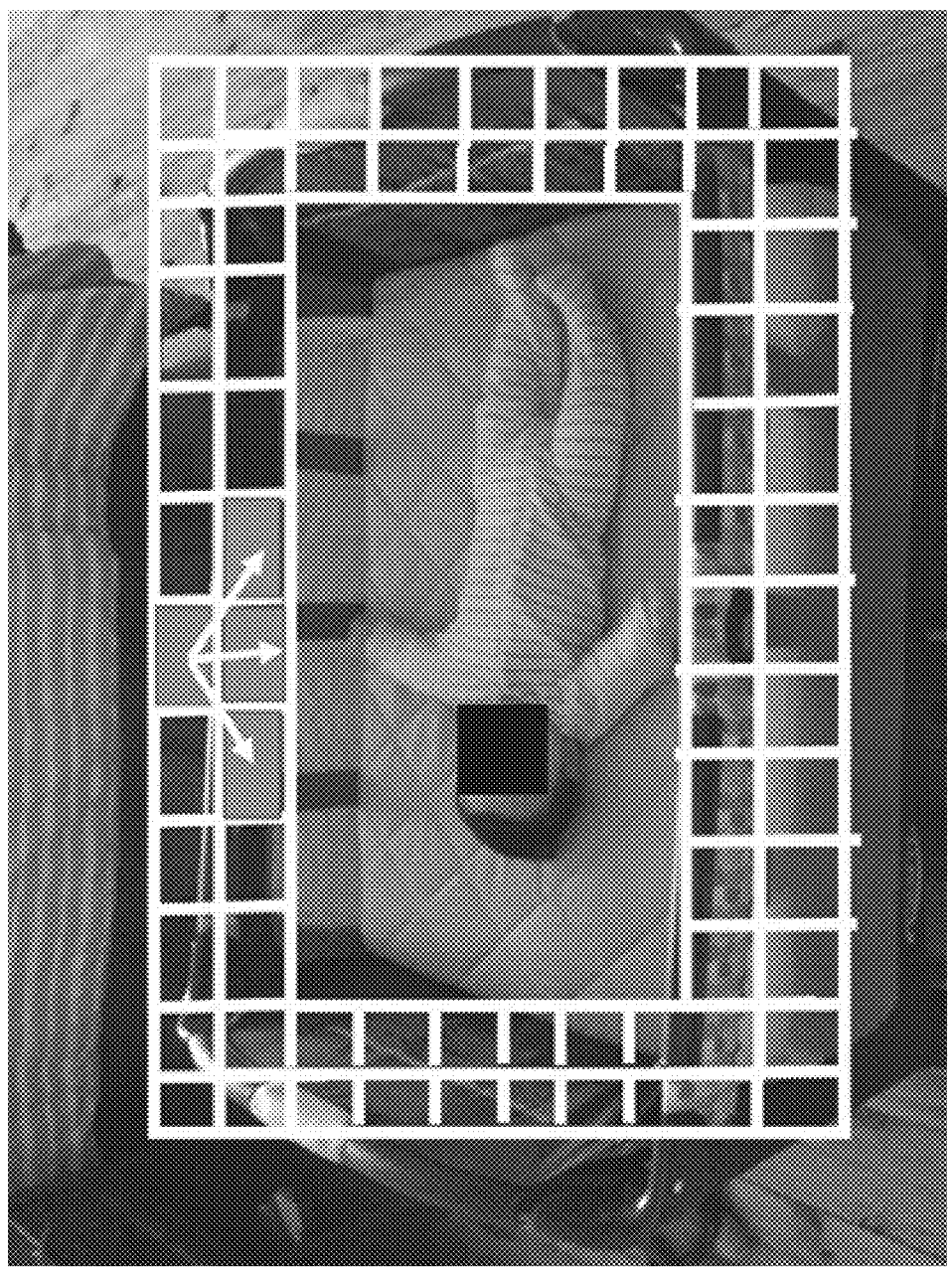
FIG. 25 shows the use of multiple perimeter regions to help identify movement of objects into or out of the perimeter or the interior region.

The perimeters can be broken down into smaller blocks as shown in FIG. 25. This would allow for finer tracking and identifying specific locations correlated with individual motion detection events.

A more specific approach can be applied to the monitoring to decrease false readings, for example when monitoring for something entering the interior region of interest. A criterion of successive motion detections of next nearest neighbors can be applied to ensure the motion is detected that fits the behavior of an object that is moving into a crib or any other region of interest. This is shown schematically in FIG. 25. This would eliminate, for example, a situation where something moves in perimeter 1 and then another object moves in perimeter 2 in different regions of the perimeter, a case where something is not moving into the interior region of interest.

An object detected moving in the perimeter can be characterized by the number of regions in which its motion is detected to give an estimate of size. The time between detections in various blocks can give information as to speed based on the known physical projection in space of each pixel. The series of blocks through which the object is detected to be moving can indicate the direction of travel.

Motion can be detected through the inventive method of array comparison of different frames. Frequencies such as fast moving objects can be filtered out by comparing frames with larger separation in time, and slower frequencies or a slower moving object can be filtered out by comparing frames with shorter separations in time. Thus, the invention can be used to isolate certain motion for detection or rejection.

Using light level changes to detect motion can cause false a positive indication of motion from things that change the illumination of the scene but are not objects moving in the field, such as fans or curtains moving from air flow. Comparing different separations in frames (hence different separations in time) can eliminate these spurious indications. For example, the slow light level changes from the natural daylight cycle would not be detected if a short time separation in frames are compared.

The inventive method can be used for various surveillance tasks. For example, one might be interested in monitoring an interior or exterior region of the home. People would be free to move about within the perimeter but if an object crosses the perimeter it would be detected.

Another example would be children playing in the backyard. One could monitor the entire backyard. The children are free to play but if a child exits the backyard the event is detected. Also if a person enters the backyard, that event is detected as well. Further, these two events can be distinguished and an appropriate alert sent. FIG. 26 shows a region in which one might monitor for people leaving or entering the region of interest. The line shows the general region where a perimeter may lie.

The invention may further include a method for determining, comparing, measuring and displaying phase.

It has been shown that intensity changes over time can be detected and correlated to physical phenomena. In many cases those signals may appear to be periodic. The periodicity can be described by frequency, amplitude and phase. In addition to the frequency and amplitude, phase is an important characteristic of the periodicity that helps temporally describe the signal and also describe one signal relative to another and relate those signals to patterns of repetitive events such as periodic motion.

The following example describes a method for extracting and analyzing phase information from time varying signals. This may be done on a single pixel level and/or for a plurality of pixels. The phase information is shown and displayed in numerous ways. Information can be gathered from the time varying signal based on the phase and its relationship to other parameters.

Example

Simplified Explicit Stepwise Procedure:

1. A time varying signal is sampled in time with a photo detector, transducer or other suitable device. This sampling represents a time sequence with appropriate resolution to correctly sample the signal of interest.

2. Multiple samples can be collected simultaneously with a plurality of pixels, e.g., with a video camera where every pixel in a single frame represents a sampling at the same point in time at different spatial locations in the scene.

3. The resulting sequence is an array of X.times.Y.times.Z (i.e., X×Y×Z) where X represents a spatial dimension, Y a spatial dimension orthogonal to X, and Z represents time.

4. FFTs are performed in the time domain along the Z axis for every pixel or element in the array. The FFT then returns a frequency spectrum for each pixel along with the amplitude and phase for each frequency.

5. The phase information for each frequency can be displayed. For a given frequency, a phase reference such as 0.degree. may be arbitrarily selected or may be associated with trigger, pulse, absolute reference, specific sample, or frame as may be preferred or selected.

6. To create a phase mask image we plot a representation of phase for a given frequency in the same pixel from which it was measured. To create a two dimensional image we first set the frequency we are interested in. For example, we may want to see the phase relationship for the 30 Hz signal. To do this we filter the image so that pixels that are in the selected phase range are white (represented numerically as 1) whereas all others are black (represented numerically as 0). The phase range may vary but for this example we will use .+- 0.5.degree. For example, if we select 30 Hz and 55.degree. then the image will show white (or 1 numerically) where a signal exists that has a frequency of 30 Hz and has a phase from 50.degree.-60.degree. This has the benefit of showing all elements of the scene that are in phase at the same frequency as they all appear white while the rest are black.

7. Taking this a step further, one can hold the frequency constant while adjusting the phase to 235.degree. which is 180.degree. out of phase of 55.degree. In mechanical systems, misalignment is typically 180.degree. out of phase across a coupling. In this manner it is possible to look at two different phase values to see if there is a phase shift indicative of misalignment. Another example would be to look at a structure such as a bridge to see if structural elements are moving in or out of phase.

8. Now if one were to start at 0.degree. and toggle to 360.degree. one would see all the different locations of the different phases for the 30 Hz signal. They would be indicated by the fact that the pixel turns white.

9. This entire process can be repeated for every frequency.

FIG. 27 outlines one approach for computing and displaying phase.

It is possible to use intensity readings to increase the information in the phase images. For example, one could take the intensity of the frequency at each pixel and multiply it by the phase mask image. Since the phase mask image is binary (if the signal is at a particular phase it is white, or valued 1, and if it is not at the selected phase it is black, or 0) the phase image acts as an image mask that will only allow the intensity values to pass if it is at the selected phase. All others will be zero. If it is in phase the intensity is preserved since it is multiplied by 1. This will create a scaled image that shows only things at a given phase and what those intensities are.

If the amplitude of the frequency of interest due to intensity changes is calibrated to a particular value then the phase mask image (that is composed of 1s or 0s denoting in or out of phase respectively) can be multiplied towards a calibrated frequency amplitude image or array. Then the resulting image displays only things in phase at a particular phase of interest at a given frequency and offers a calibrated value. That calibrated value may be from anything that is causing the signal levels to change. It could be temperature variation from thermal IR imagers, displacement from moving features in a visible image or even variations in absorption levels through a transmitted medium.

For a measurement made with video imagery the phase may be referenced simply to the first image taken so that all phase readings are relative to the first image. However it is possible to synchronize the phase readings to another signal. This could be a trigger pulse or even a time varying optical signal in the scene of the imager.

Exposure modes on imaging sensors are often different. Two types of modes are global and rolling shutters. Global shutters expose every pixel at the same time. Rolling shutters expose lines of the sensor at different times. In the case of a global shutter all pixels are exposed simultaneously so the phase relationship is preserved across the sensor. In the case of a rolling shutter there are variations in the timing of exposure from pixel to pixel. It is possible to realign temporal signals based on the known delay between pixels after they are read from the imaging sensor. By accounting for this offset we can preserve the relationship of phase across all pixels.

It is possible to use the phase information in a noise reduction manner. For example, in the event of a phase image mask where the array or image is binary (1s for in phase, 0s for out of phase) one can reject all pixels out of phase at a given frequency and given phase. When exploring an image, if many pixels effectively "turn off", it eliminates much background noise in the scene and makes detection much easier. This may be advantageous, for example, in a cluttered field or where many time-varying signals exist. Additionally, one can reduce noise by multiplying the phase mask image by the frequency intensity image and setting an intensity threshold below which the pixel is set to 0 or not represented in the scaling.

Mechanical or anelastic properties that have particular phase properties can be imaged and detected with the described technique. Phase relationship information can be exploited with the described technique to reveal physical parameters or other properties.

By cycling through all the phase mask images at a given frequency, traveling waves may be seen in the sequence of images created.

Different areas of the array or frame of the same or different phase mask images may be compared to show certain areas of interest indicating anomalies, e.g., one area that is out of phase with the rest. Or, these areas could be compared to find patterns indicative of physical phenomenon.

The following five exemplary cases demonstrate some useful applications of this aspect of the present invention.

One use of phase presentation as described herein is to determine and to graphically display absolute or relative timing characteristics and patterns.

A second example is to demonstrate a modulation or a beat frequency or other characteristic which may correspond with a movement of an object of interest.

A third example is to represent a leading or a lagging event sequence made evident mathematically or graphically using techniques described herein. Again, this leading or lagging event sequence may be related to a movement sequence of an object of interest.

A fourth example of the present invention is to characterize highly repetitive displacement patterns such as a static or a dynamic constructive and destructive interference pattern resulting from multiple vibration wave fronts. The multiple fronts each typically originate from a point, line, or area of reflection, or originate from a point, line, or area vibration energy source. This technique may be used to discern false or positive indications. For example, a false indication may be found from a highly repetitive pattern which is more likely produced by a machine than a living being.

Vital signs of living beings, people and animals, may be interrelated and phase related. For example, a repetitive breathing may show leading, lagging, or concurrent phase relationships between related events such as vapor or air inhaled and exhaled, sequential chest and thorax movements, temperature oscillations, and color variations. Phase of an edge from the chest motion can be characterized with an upward or downward motion (black/white edge or white/black edge) by analyzing the two sides of the edge. This motion can then be correlated with thermal data as temperatures cool (downward motion in waveform) on inhale at the nostril or as temperatures rise (upward motion in waveform) on exhale at the nostril. The relationship between the phase data can be used to indicate false positives/negatives or determine the chest vs nostril location. For another example, a phase relationship measurement may characterize physiology of blood flowing through veins, arteries, and capillaries.

As described earlier, one can use IR images to observe the breathing cycle by temperature changes around the nose. It will be appreciated that such a temperature cycle will be either in phase or 180.degree. out of phase with the chest movement.

The GUI may further include a video display in which motions have been visually amplified using the method of amplification taught in Applicant's co-pending application "Method of adaptive array comparison for the detection and characterization of periodic motion," U.S. Publication No. 2016/0217588.

The invention may further include various ways of interfacing the output signal directly with existing hardware that is typically employed in clinical settings and sleep laboratories.

Example

Figure 28:
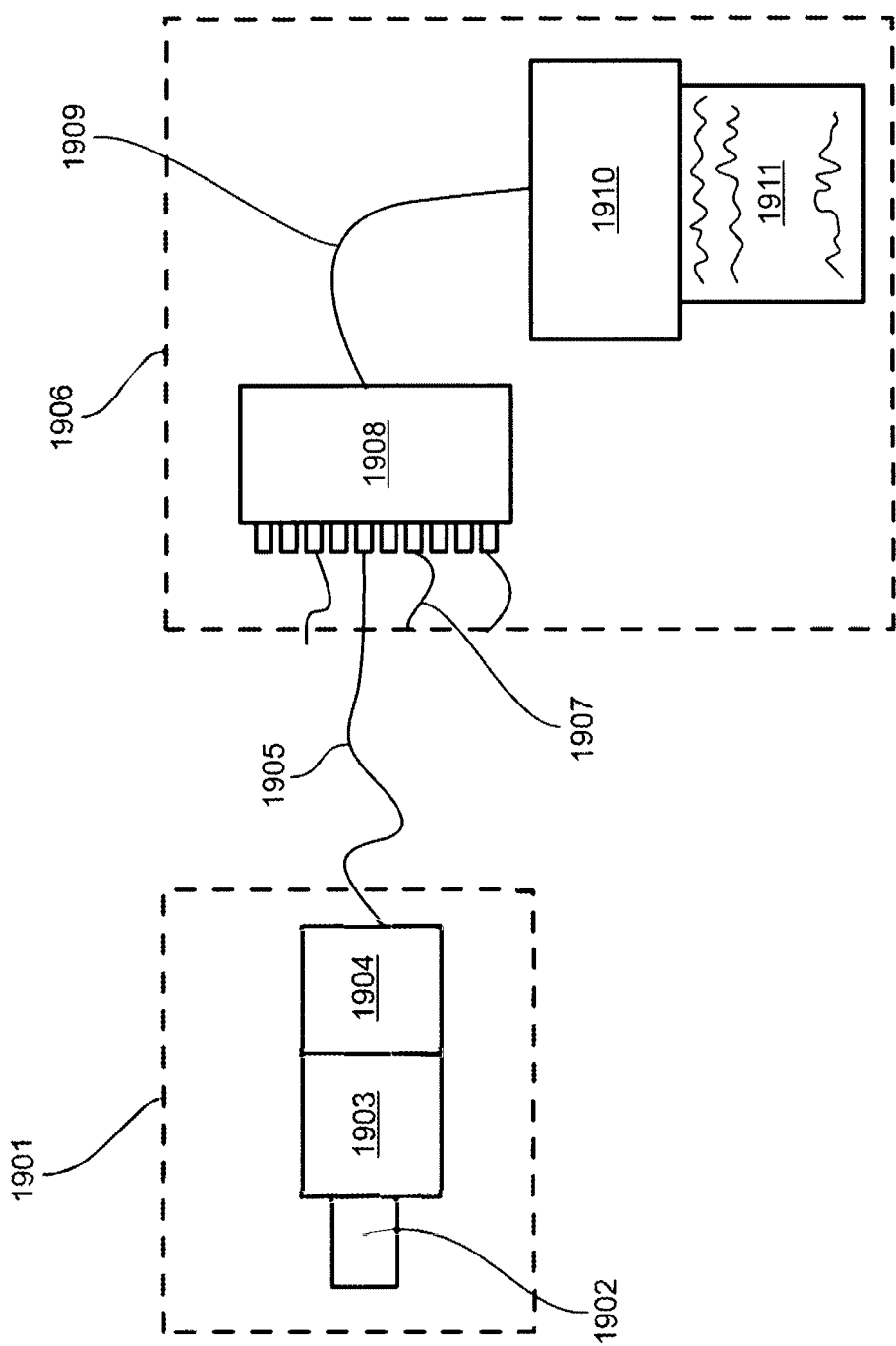
FIG. 28 illustrates schematically one configuration to interface the invention with existing sleep center hardware and methods.

FIG. 28 illustrates schematically a typical polysomnographic data acquisition and analysis system 1906, including an amplifier module 1908 capable of accepting inputs 1907 from a variety of sensors that are attached to the patient. One such amplifier is the JE-921 [Nihon Kohden Europe, Rosbach, Germany], which accepts 20 unipolar and 14 bipolar inputs. Output from amplifier 1908 passes via link 1909 to the system monitoring hardware and software 1910 [e.g., the Polysmith™ PSG acquisition and analysis program, Nihon Kohden Europe] for output in a user interface 1911 or other suitable format.

The inventive system 1901 comprises an imager or camera 1902, a CPU 1903 for processing the image data and transforming image data to movement and respiration measurements, and an output module 1904 for transforming the information into a suitable output signal, which is then delivered via a wired or wireless link 1905 to one of the input jacks on amplifier module 1908. The output signal from system 1901 will typically be conditioned to a suitable range for amplifier 1908 (e.g., +/−2 VDC).

It will be appreciated that when used in this manner, the inventive system 1901 is conveniently substituted directly for an existing sensor for monitoring chest movement, which in most cases is a belt placed around the patient's chest. So it eliminates the restraint of the chest belt while at the same time, offering direct "plug and play" input into the existing laboratory infrastructure and data archiving systems. Because sleep centers often use video cameras simply to record the general movements of the patient over the course of the night, a further advantage of the invention when used in the manner shown in FIG. 28 is that the raw video stream from imager 1902 can be archived and serve as the video of record for a particular session.

Comparison of the invention with traditional "frame difference" methods.

It will be understood that although the invention involves subtracting pixel values at one time from those at another time, the inventive Adaptive Array Comparison method differs considerably from traditional techniques broadly referred to as "frame difference" methods in at least the following ways:

1. Adaptive Array Comparison specifically targets individual frames at particular references for the purpose of exploiting periodic signals. 2. Adaptive Array Comparison adapts to the signal, learns from the signal and modifies its approach. 3. Adaptive Array Comparison targets periodic signals to isolate them from the background. 4. Adaptive Array Comparison relates to time intervals based on signal of interest. 5. Adaptive Array Comparison isolates particular phases of motions, max and mins in its approach. 6. Adaptive Array Comparison is an iterative process and involves comparison of the results of those iterative steps. 7. Adaptive Array Comparison is a temporally based and links arrays to particular points in time. 8. Adaptive Array Comparison generally involves multiple comparison of arrays over time and relies on the cumulative result.

What is claimed is:

1. A monitoring system, comprising:
a data analysis system including processor and memory for storing video image files, wherein each video file comprises a sequence of video frames of a scene that are divided into pixels defined by two or more spatial coordinates within each frame;
a computer program operating in said processor to:
identify at least a first set of pixels in said video frames that are associated with a first individual based on an intensity value of either light intensity changes from periodic motions of the first individual or intensity changes in thermal IR from temperature changes associated with at least one of said first individual's vital signs;
measure intensity changes of the first set of pixels to monitor one or more vital signs of the first individual; and
identify at least a second set of pixels associated with the first individual that the system automatically switches to when changes occur in the scene which compromise the measurement obtained from the first set of pixels in order to reduce gaps in the vital sign measurement or false alarms from erroneous readings.

2. The system of claim 1, wherein the monitored vital sign is chosen from the group consisting of: respiration rate; respiration effort; respiration waveform; pulse rate; pulse waveform; pulse transit time; temperature; sleep quality index; and state of stress.

3. The system of claim 1, wherein the computer program operates to locate the second set of pixels based upon spatial correlation of the first set of pixels to the second set of pixels or proximity requirements with respect to the first set of pixels such that multiple measurements of the first individual's one or more monitored vital signs exist.

4. The system of claim 1, wherein the computer program operates to locate the second set of pixels based upon the frequency of maximum variation of intensity falling within a permissible range suited to the first individual's monitored vital sign, such that multiple measurements of the first individual's one or more monitored vital signs exist.

5. The system of claim 1, wherein the computer program operates to locate the second set of pixels which are in phase with the first set of pixels.

6. The system of claim 1, wherein the video files are acquired from one or more of multiple cameras, a combination of visible and IR cameras, or multiple wavelengths from a single camera.

7. The system of claim 1, wherein a boundary set of pixels is determined which form a boundary around the monitored subject individual such that the transition of the first individual exiting the boundary automatically creates an alarm.

8. The system of claim 7, wherein monitoring of the first individual occurs only within the boundary set of pixels.

9. The system of claim 1, wherein a boundary set of pixels is determined which forms a boundary around the first individual such that entry of a second individual within the boundary automatically creates an alarm.

10. The system of claim 7, wherein a user defines the boundary set of pixels using a graphical interface.

11. The system of claim 1,
wherein the computer program operates to identify at least a third set of pixels from a second individual associated with one or more vital signs of the second individual, based on an intensity value of either light intensity changes from periodic motions of the second individual or intensity changes in thermal IR from temperature changes associated with at least one of said second individual's vital signs.

12. The system of claim 11, wherein the monitored vital sign is chosen from the group consisting of: respiration rate; respiration effort; respiration waveform; pulse rate; pulse waveform; pulse transit time; temperature; sleep quality index; and state of stress.

13. The system of claim 11, wherein video image files are obtained with a camera that is not located in the same room and the observation is made through a transparent and/or semitransparent barrier such as in the event a quarantine is necessary for the first and second individuals.

14. The system of claim 11, wherein the system is configured to provide output signals to control temperature or other environmental conditions in the room.

15. A monitoring system, comprising:
a data analysis system including processor and memory for storing video image files, wherein each video file comprises a sequence of video frames of a scene that are divided into pixels defined by two or more spatial coordinates within each frame; and
a computer program operating in said processor to:
identify a first set of pixels in said video frames based on an intensity value of either light intensity changes from periodic motions or intensity changes in thermal IR from temperature changes of a subject individual's motion, wherein measured intensity changes of the first set of pixels is associated with one or more measured vital signs of said subject individual which are chosen from the group consisting of: respiration rate; respiration effort; respiration waveform; pulse rate; pulse waveform; pulse transit time; temperature; sleep quality index; and state of stress;
identify at least a second set of pixels associated with the subject individual that the system automatically switches to when changes occur in the scene which compromise the measurement obtained from the first set of pixels in order to reduce gaps in the vital sign measurement or false alarms from erroneous readings; and
match at least one characteristic diagnostic template to a waveform of any of the measured vital signs to identify specific events of clinical importance or associated with measures of sleep quality or stress and capture video image files associated with said waveforms.

16. The system of claim 15, wherein the system is configured to identify central versus obstructive sleep apnea patterns in the subject individual.

17. The system of claim 15, further comprising a device for acquiring video image files, wherein the device is a stationary camera positioned at a prescribed distance recording the subject individual, and the system is configured to identify one or more of tremors, spasms, seizures, and pseudoseizures in the subject individual.

18. The system of claim 15, further comprising a device for acquiring video image files, wherein the device is a camera and the subject individual is a user focusing the camera on a fixed object, and wherein the system is configured to identify one or more of tremors, spasms, seizures, and pseudoseizures experienced by the patient user while focusing the camera on the fixed object.

19. The system of claim 15, wherein the subject individual is an infant or bedridden individual, and wherein the system is configured to identify at least one of restless sleep conditions and breathing cessation, and to alert a responsible caregiver.

20. The system of claim 1, wherein the second set of pixels provides a higher confidence of the accuracy of the measured vital sign or replaces the measurement provided by the primary set of pixels when changes occur in the scene which compromise the measurement from the first set of pixels.

21. The system of claim 9, wherein a user defines the boundary set of pixels using a graphical interface.

* * * * *